(12) United States Patent
Kono

(10) Patent No.: US 8,557,875 B2
(45) Date of Patent: Oct. 15, 2013

(54) GENE TRANSFER AGENT COMPOSITION CONTAINING POLYAMIDOAMINE DENDRON

(75) Inventor: Kenji Kono, Sakai (JP)

(73) Assignee: Public University Corporation Osaka Prefecture University, Sakai-shi (JP)

( * ) Notice: Subject to any disclaimer, the term of this patent is extended or adjusted under 35 U.S.C. 154(b) by 24 days.

(21) Appl. No.: 13/289,423

(22) Filed: Nov. 4, 2011

(65) Prior Publication Data

US 2012/0053233 A1 Mar. 1, 2012

Related U.S. Application Data

(63) Continuation-in-part of application No. PCT/JP2010/057788, filed on May 7, 2010.

(30) Foreign Application Priority Data

May 7, 2009 (JP) ................................ 2009-112969

(51) Int. Cl.
*A61K 47/16* (2006.01)
*A61K 9/14* (2006.01)

(52) U.S. Cl.
USPC .............................. 514/788; 424/486; 977/754

(58) Field of Classification Search
None
See application file for complete search history.

(56) References Cited

FOREIGN PATENT DOCUMENTS

| JP | 2001048851 | * | 2/2001 |
| JP | 2004-159504 A | | 6/2004 |
| WO | WO 2008/139855 A1 | | 11/2008 |
| WO | WO 2008/141357 A1 | | 11/2008 |

OTHER PUBLICATIONS

Nakajima et al., *Abstracts of the 31st Annual Meeting of the Japanese Society of Biomaterials*, 31: 420, Item 2P102 (Nov. 16, 2009), English translation and English language search report.
Nakajima et al., *Abstracts of the Society of Polymer Science, Japan*, 58(1): 1935, Item 1Ph146 (May 12, 2009), English translation and English language search report.
Takahashi et al., *Bioconjugate Chemistry*, 18: 1349-1354 (2007).
Japanese Patent Office, International Search Report in International Patent Application No. PCT/JP2010/057788 (Jun. 1, 2010), English translation.
European Patent Office, Extended European Search Report in European Patent Application No. 10772186.2 (Nov. 9, 2012).

* cited by examiner

*Primary Examiner* — Doug Schultz
(74) *Attorney, Agent, or Firm* — Leydig, Voit & Mayer, Ltd.

(57) ABSTRACT

The present invention provides a gene transfer agent, a gene transfer kit, and a gene transfer method excellent in safety and transfer efficiency. Specifically, the present invention provides a gene transfer agent composition, the gene transfer agent composition including a compound represented by any one of the following formulae DL-G1 to DL-G4: DL-G1: $R^1R^2NX(XH_2)_2$; DL-G2: $R^1R^2NX(X(XH_2)_2)_2$; DL-G3: $R^1R^2NX(X(X(XH_2)_2)_2)_2$; and DL-G4: $R^1R^2NX(X(X(X(XH_2)_2)_2)_2)_2$ (X represents $-CH_2CH_2CONHCH_2CH_2N-$), in which: $R^1$ represents an unsaturated long-chain aliphatic group; and $R^2$ represents an unsaturated long-chain aliphatic group or a saturated long-chain aliphatic group in the formulae.

6 Claims, 15 Drawing Sheets

GENE TRANSFER AGENT COMPOSITION CONTAINING POLYAMIDOAMINE DENDRON

CROSS-REFERENCE TO RELATED APPLICATIONS

This patent application is a continuation-in-part of co-pending International Patent Application PCT/JP2010/057788, which designated the U.S. and was filed on May 7, 2010. This application claims priority to the specification of Japanese Patent Application No. 2009-112969 which was filed on May 10, 2009, and the specification of International Patent Application PCT/JP2010/057788 which was filed on May 7, 2010, the disclosures of which are incorporated herein by reference in its entirety.

TECHNICAL FIELD

The present invention relates to a gene transfer agent, a gene transfer kit, and a gene transfer method.

BACKGROUND ART

Viral vectors, known as gene transfer agents with high efficiency, are used for genetic therapies and the like. However, there are reports that viral vectors have severe side effects leading to death in clinical applications. Hence, a gene transfer agent with high safety has been demanded.

Although non-viral vectors show higher safety than that of viral vectors, non-viral vectors have a drawback in that their gene transfer efficiency is lower.

The inventor of the present invention has already developed, as an excellent gene transfer agent composition that can solve the above-mentioned problem, a gene transfer agent composition containing a polyamidoamine dendron (Patent Literature 1).

CITATION LIST

Patent Literature

[PTL 1] JP 2004-159504 A

SUMMARY OF INVENTION

Technical Problem

An object of the present invention is to provide a gene transfer agent, a gene transfer kit, and a gene transfer method excellent in safety and transfer efficiency. In particular, another object of the present invention is to provide an improved gene transfer agent composition containing polyamidoamine dendron.

Solution to Problem

The present invention provides the following gene transfer agent, gene transfer kit, and gene transfer method.

Item 1. A gene transfer agent composition comprising a compound represented by any one of the following formulae DL-G1 to DL-G4:

$R^1R^2NX(XH_2)_2$;      DL-G1:

$R^1R^2NX(X(XH_2)_2)_2$;      DL-G2:

$R^1R^2NX(X(X(XH_2)_2)_2)_2$;      DL-G3:

and $R^1R^2NX(X(X(X(XH_2)_2)_2)_2)_2$,      DL-G4:

(X represents $-CH_2CH_2CONHCH_2CH_2N-$)
in which:
$R^1$ represents an unsaturated long-chain aliphatic group; and
$R^2$ represents an unsaturated long-chain aliphatic group or a saturated long-chain aliphatic group in the above-mentioned formulae.

Item 2. The gene transfer agent composition according to Item 1, in which the long-chain aliphatic group comprises an aliphatic group having 10 to 22 carbon atoms.

Item 3. The gene transfer agent composition according to Item 1, in which the unsaturated long-chain aliphatic group is a hexadecenyl group, an octadecenyl group, an octadecadienyl group, an octadecatrienyl group, an icosatrienyl group, an icosatetraenyl group, an octadecatrienyl group, an icosapentaenyl group, or a docosahexaenyl group.

Item 4. The gene transfer agent composition according to any one of Items 1 to 3, further comprising a phospholipid.

Item 5. The gene transfer agent composition according to Item 4, in which the phospholipid comprises DOPE.

Item 6. A method of transferring a gene into a cell, comprising applying the gene transfer agent composition according to any one of Items 1 to 5 and a gene to a cell in vitro or in vivo (provided that a human is excluded).

Item 7. A gene transfer kit, including the gene transfer agent composition according to any one of Items 1 to 5.

Advantageous Effects of Invention

According to the present invention, it is possible to provide a gene transfer agent with significantly improved gene transfer efficiency and significantly reduced cytotoxicity as compared to a conventional gene transfer agent. Therefore, it is possible to provide a gene transfer technology that is excellent in both transfer efficiency and safety, and that can find a wide range of practical uses.

2C18 or DL-G1-2C18-U2 lipoplexes with various N/P ratios. The cells (5×10) were treated with a lipoplex containing 1 µg of DNA in a serum-free medium. N and P represent an equivalent of a primary amino group in a lipid and an equivalent of a DNA phosphate, respectively.

Figure 8:
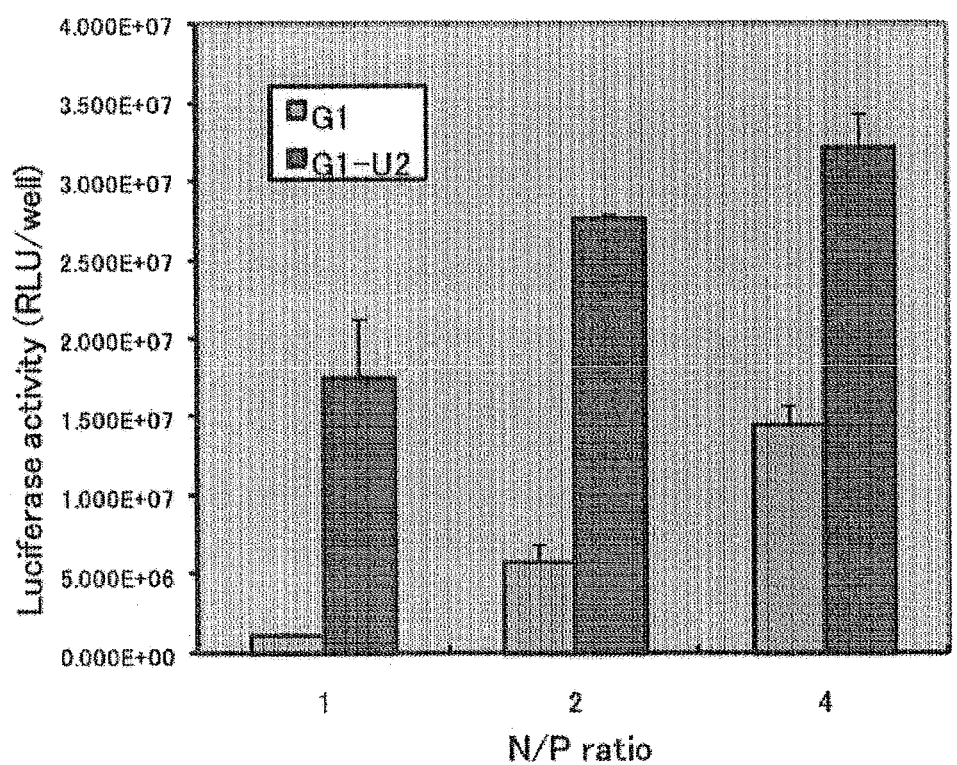

FIG. 8 is a graph showing luciferase activities (g of luciferase/well) of CV1 cells treated with DL-G1-2C18 or DL-G1-2C18-U2 lipoplexes with various N/P ratios. The cells (5×10$^4$) were treated with a lipoplex containing 1 µg of DNA in a serum-free medium. N and P represent an equivalent of a primary amino group in a lipid and an equivalent of a DNA phosphate, respectively.

Figure 9:
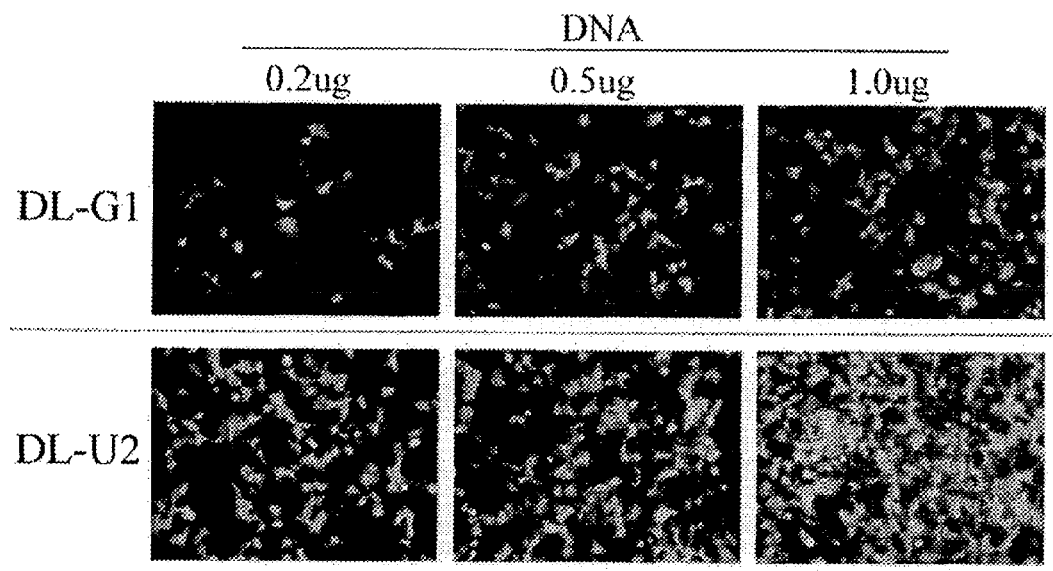

FIG. 9 is 100× microscopic images showing the results of transfection of a GFP-expression plasmid into COS7 cells using DL-G1-2C18-U2 (DL-U2) in which both of $R^1$ and $R^2$ represent unsaturated alkyl groups, and DL-G1-2C18 (DL-G1) in which both of $R^1$ and $R^2$ represent saturated alkyl groups.

Figure 10:
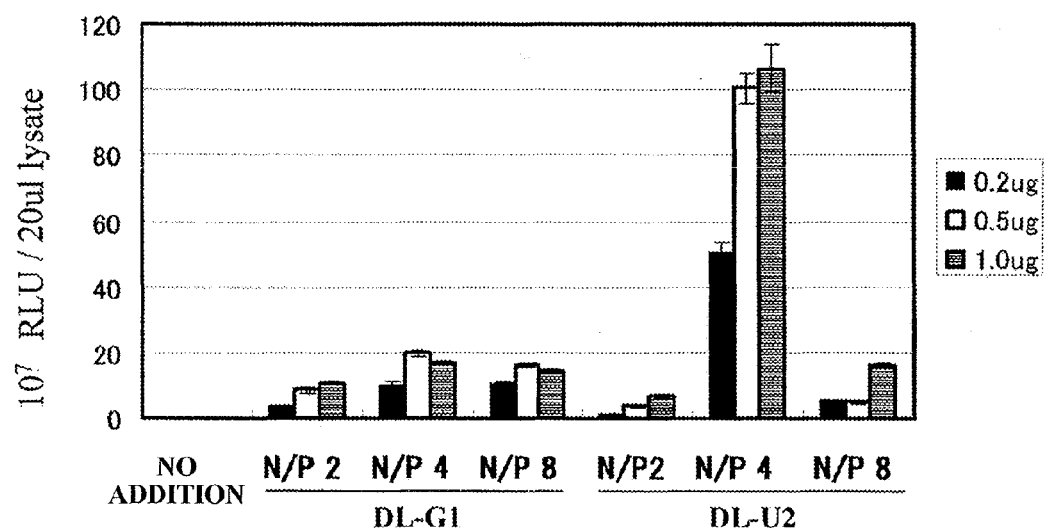

FIG. 10 is a graph showing luciferase activities measured after transfection of a GFP-expression plasmid into COS7 cells using, individually, DL-U2 and DL-G1.

Figure 11:
Figure 11:
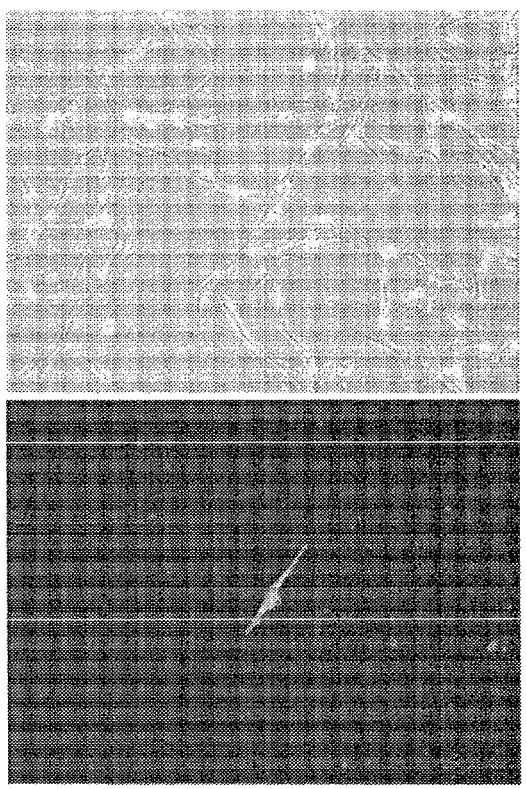

FIG. 11 is 100× microscopic images showing the results of transfection of a GFP-expression plasmid into NHDH-ad cells using, individually, DL-U2 and DL-G1.

Figure 12:
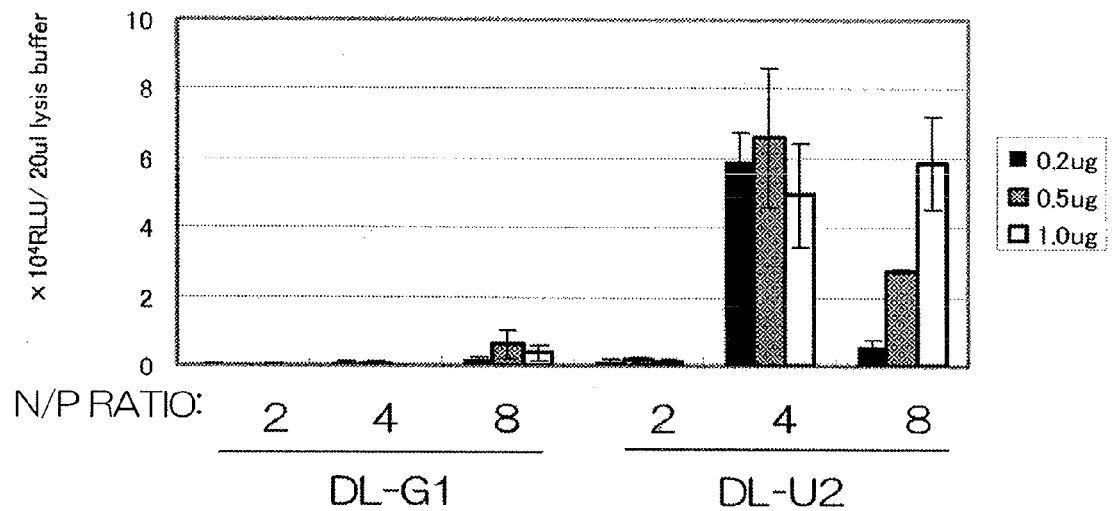

FIG. 12 is a graph showing luciferase activities measured after transfection of a GFP-expression plasmid into NHDH-ad cells using, individually, DL-U2 and DL-G1.

Figure 13:
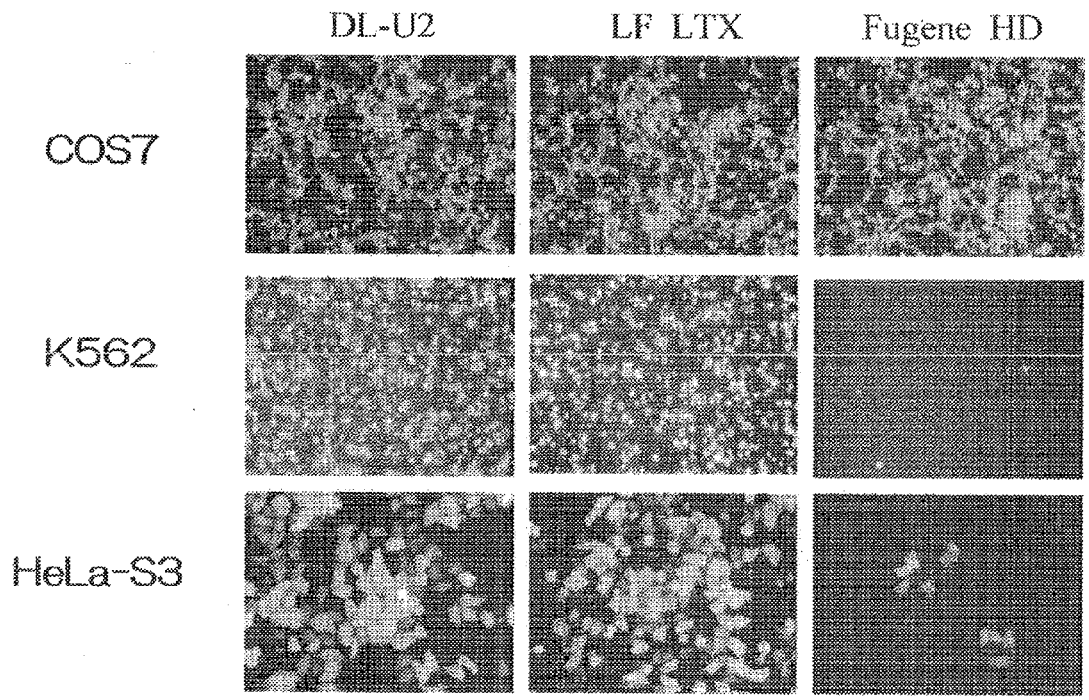

FIG. 13 is microscopic images showing the results of transfection of a GFP-expression plasmid into various types of cells using, individually, DL-U2 and other companies' products (LF LTX and FuGENE HD). The microscopic images are 100× microscopic images for COS7 cells and Hela-S3 cells, and 200× microscopic images for K562 cells.

Figure 14:
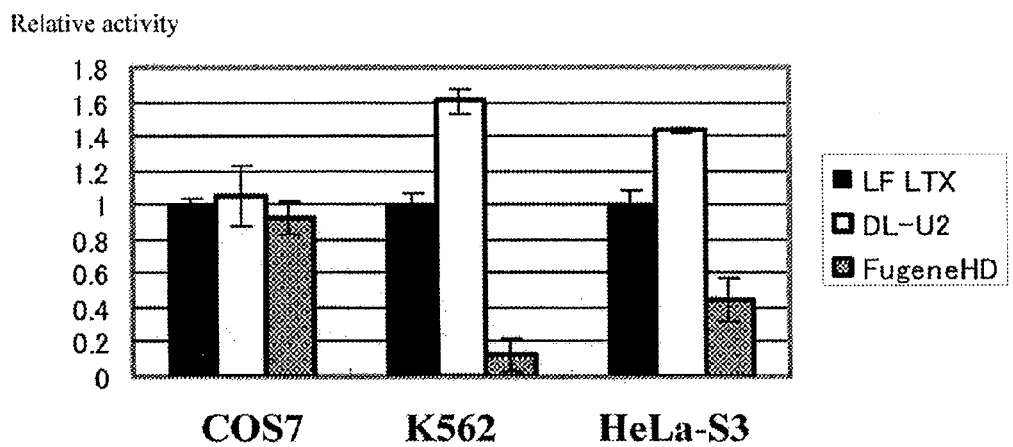

FIG. 14 is a graph showing relative values of luciferase activity levels with respect to a value of LF LTX defined as 1 in the case where a GFP-expression plasmid is transfected into various types of cells using, individually, DL-U2 and other companies' products (LF LTX and FuGENE HD).

Figure 15:
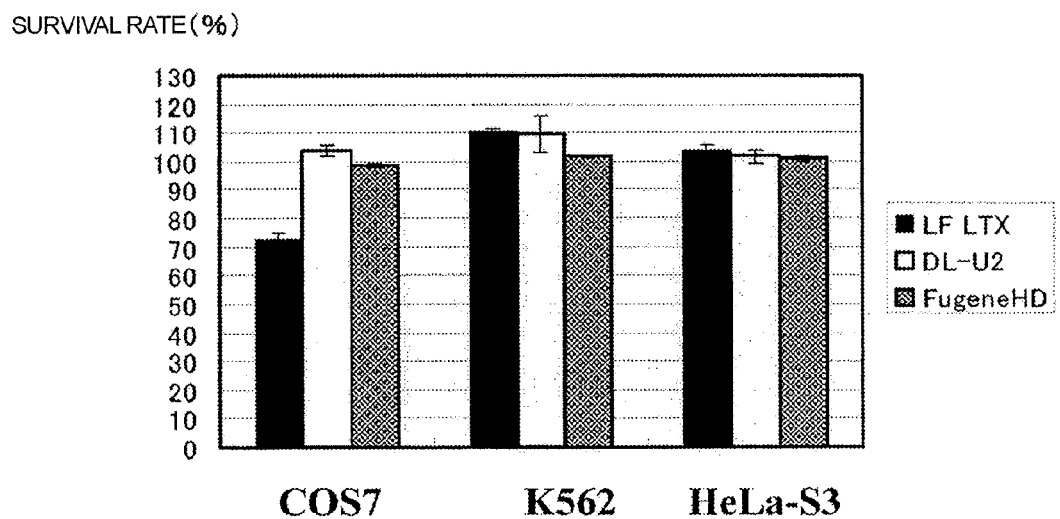

FIG. 15 is a graph showing the results of cytotoxic evaluation in the case where a GFP-expression plasmid is transfected into various types of cells using, individually DL-U2 and other companies' products (LF LTX and FuGENE HD).

Figure 16:
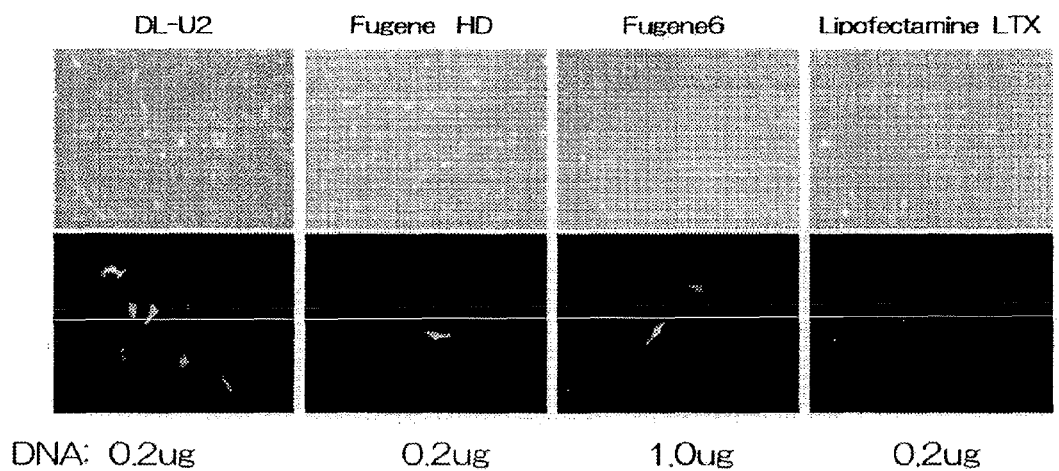

FIG. 16 is microscopic images showing the results of transfection of a GFP-expression plasmid into NHDH-ad cells using, individually, DL-U2 and other companies' products (FuGENE HD, FuGENE 6, and LF LTX). The microscopic images are 100× microscopic images for COS7 cells and Hela-S3 cells, and 200× microscopic images for K562 cells.

Figure 17:
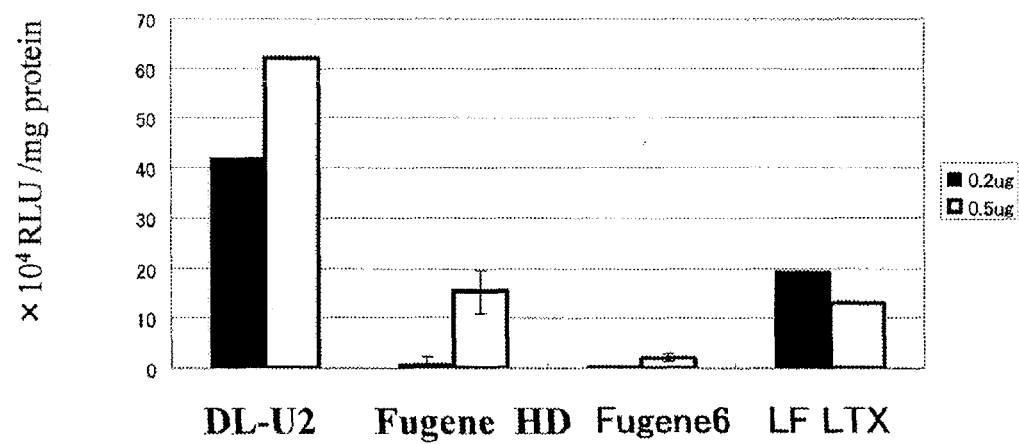

FIG. 17 is a graph showing luciferase activity levels in the case where a GFP-expression plasmid is transfected into NHDH-ad cells using, individually, DL-U2 and other companies' products (FuGENE HD, FuGENE 6, and LF LTX).

Figure 18:
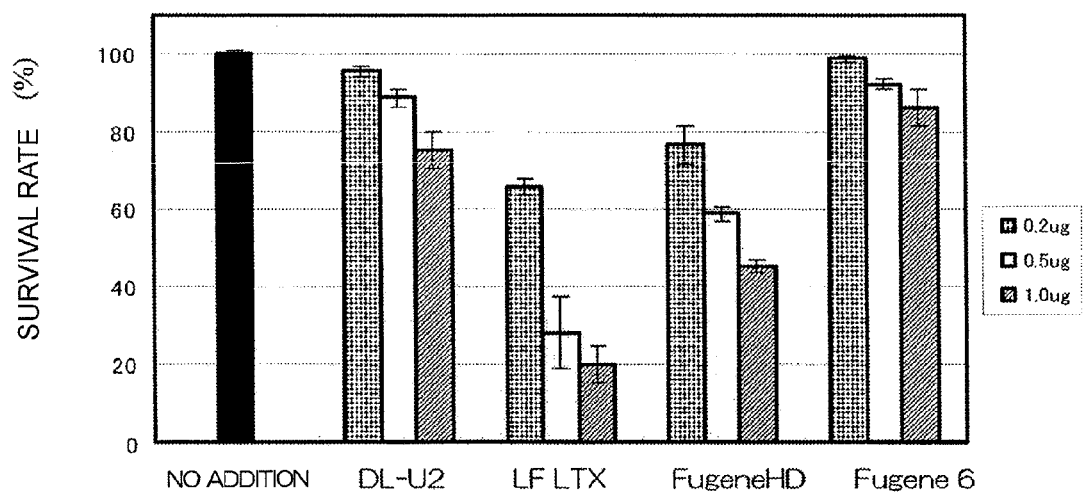

FIG. 18 is a graph showing the results of cytotoxic evaluation in the case where a GFP-expression plasmid is transfected into NHDH-ad cells using, individually, DL-U2 and other companies' products (FuGENE HD, FuGENE 6, and LF LTX).

Figure 19:
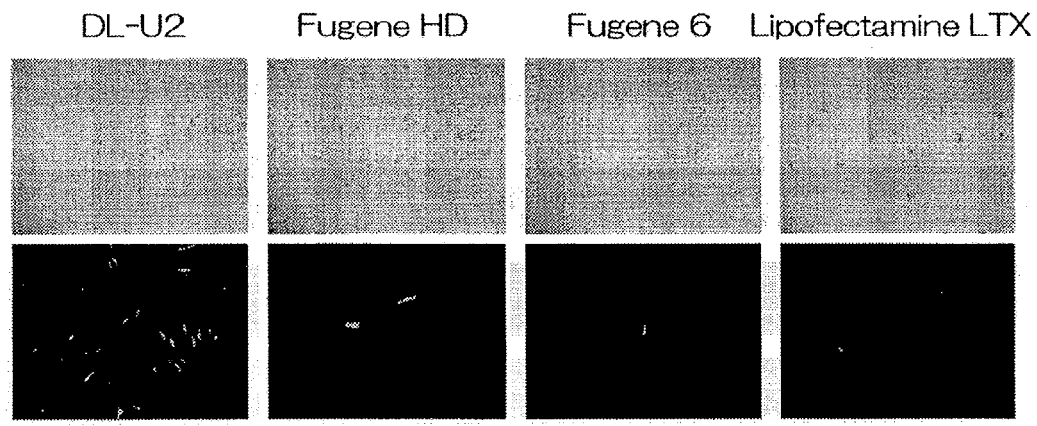

FIG. 19 is microscopic images showing the results of multiple transfection of a GFP-expression plasmid into NHDH-ad cells using, individually, DL-U2 and other companies' products (FuGENE HD, FuGENE 6, and LF LTX). All of the microscopic images are 40× microscopic images.

Figure 20:
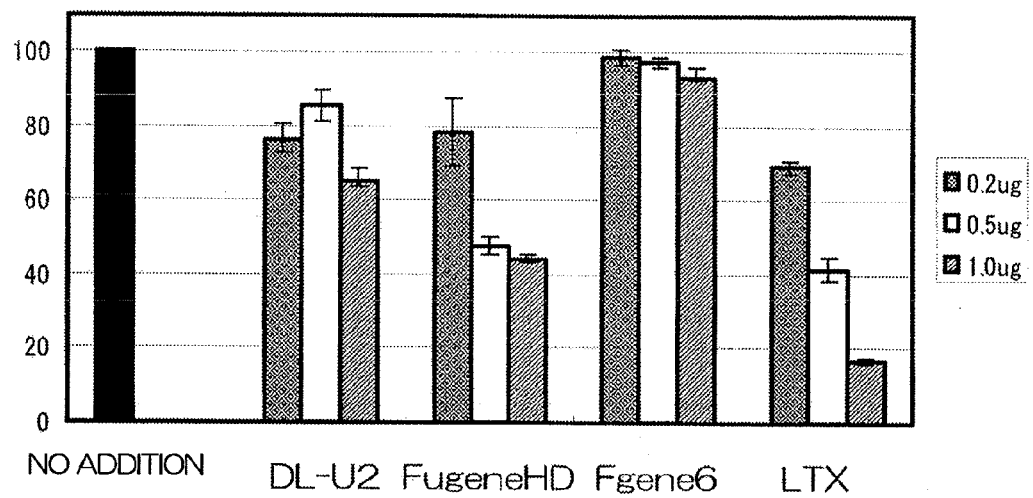

FIG. 20 is a graph showing the results of cytotoxic evaluation in the case where multiple transfection of a GFP-expression plasmid into NHDH-ad cells is performed using, individually, DL-U2 and other companies' products (FuGENE HD, FuGENE 6, and LF LTX).

Figure 21:
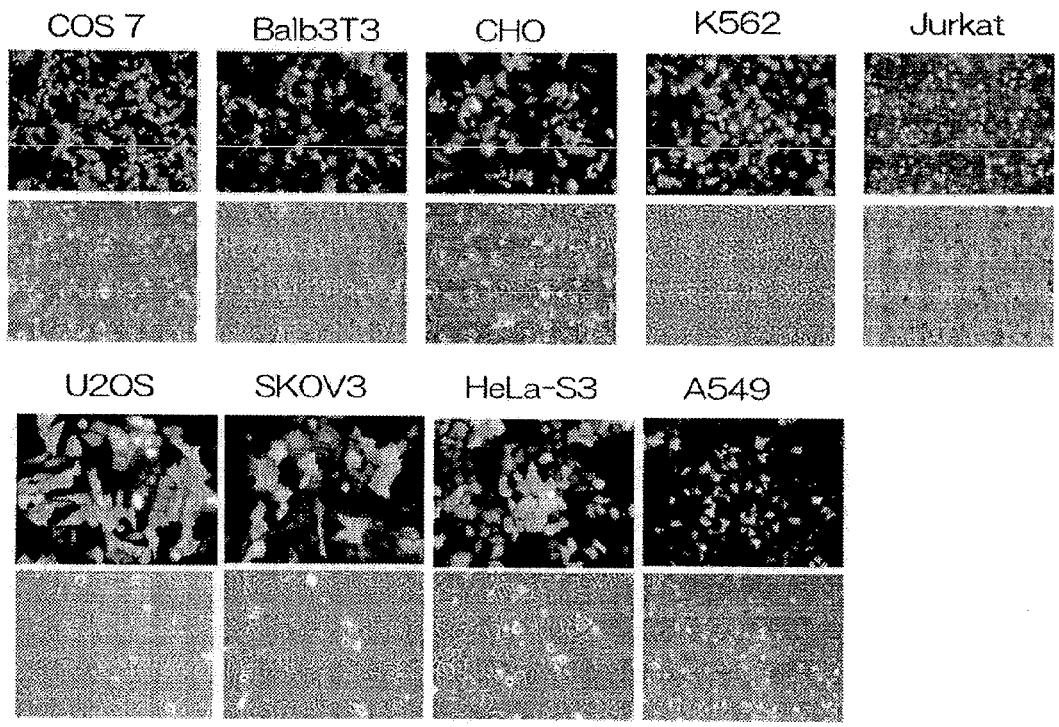

FIG. 21 is microscopic images showing the results of transfection of a GFP-expression plasmid into various types of cells using DL-U2. The magnifications of the microscopic images are 100× for A549 cells, COST cells, Jurkat cells, and Balb3T3 cells; and 200× for other cells.

DESCRIPTION OF EMBODIMENTS

The gene transfer agent composition of the present invention is a gene transfer agent composition comprising a compound represented by any one of the following formulae DL-G1 to DL-G4:

$$R^1R^2NX(XH_2)_2; \qquad \text{DL-G1:}$$

$$R^1R^2NX(X(XH_2)_2)_2; \qquad \text{DL-G2:}$$

$$R^1R^2NX(X(X(XH_2)_2)_2)_2; \qquad \text{DL-G3:}$$

and $$R^1R^2NX(X(X(X(XH_2)_2)_2)_2)_2, \qquad \text{DL-G4:}$$

(X represents —CH$_2$CH$_2$CONHCH$_2$CH$_2$N—)
in which:
$R^1$ represents an unsaturated long-chain aliphatic group; and
$R^2$ represents an unsaturated long-chain aliphatic group or a saturated long-chain aliphatic group in the above-mentioned formulae.

1. Description of X

X represents —CH$_2$CH$_2$CONHCH$_2$CH$_2$N—. N at a terminal thereof usually has two hydrogen atoms; however, one of the hydrogen atoms may be substituted with a hydrophobic amino acid such as leucine, valine, isoleucine, norleucine, phenylalanine, or tyrosine.

2. Description of $R^1$ and $R^2$ $R^1$ represents an unsaturated long-chain aliphatic group.

$R^2$ represents an unsaturated long-chain aliphatic group or a saturated long-chain aliphatic group.

The saturated long-chain aliphatic group and the unsaturated long-chain aliphatic group are collectively referred to as a long-chain aliphatic group.

The long-chain aliphatic group may be an aliphatic group of natural origin, an aliphatic group obtained by modifying the aliphatic group of natural origin, or an artificially synthesized aliphatic group.

The long-chain aliphatic group is not limited, as long as it is a chain aliphatic group having a long chain.

The number of carbons in the long-chain aliphatic group is not limited, as long as the main chain thereof is a long chain. The number of carbons in the main chain is preferably 8 to 30, more preferably 10 to 22, still more preferably 12 to 20.

The long-chain aliphatic group may be branched. It should be noted that the main chain is determined according to IUPAC nomenclature. When determination is difficult or impossible, the main chain is determined according to a method pursuant to the nomenclature.

The long-chain aliphatic group may be one in which at least one carbon atom is substituted by a heteroatom in a hydrocarbon group. The heteroatom refers to at least one atom selected from the group consisting of an oxygen atom, a nitrogen atom, and a sulfur atom. Specific examples of the long-chain aliphatic group include a hydrocarbon group, an oxygen-containing hydrocarbon group, a nitrogen-containing hydrocarbon group, and a sulfur-containing hydrocarbon group.

The hydrocarbon group is an alkyl group, an alkenyl group, or an alkynyl group.

Examples of the oxygen-containing hydrocarbon group include an oxygen-containing hydrocarbon group having at least one kind of bond selected from the group consisting of an ether bond and a carbonyl bond. Examples of the oxygen-containing hydrocarbon group having a carbonyl bond include a group having at least one kind of structure selected from the group consisting of an aldehyde, a ketone, a carboxylate, an ester, an amide, an enone, an acid chloride, and an anhydride.

Examples of the nitrogen-containing hydrocarbon group include a nitrogen-containing hydrocarbon group having at least one kind of structure selected from the group consisting of a nitrile, an amine, an amide, and an imide.

Examples of the sulfur-containing hydrocarbon group include a sulfur-containing hydrocarbon group having at least one kind of bond selected from the group consisting of a thiol, a thioether, a thioacetal, a sulfide, a disulfide, a dithiocarboxylate, a thioester, a thioketone, a thioaldehyde, a thiocarbamate, a thiourethane, a phosphine sulfide, a thiophosphate, a thiophosphonate, a sulfonate, a sulfone, and a sulfonamide.

The long-chain aliphatic group may further have at least one substituent in the group having the structure as exemplified above. The substituent preferably shows hydrophobicity. Examples of the substituent include a phenyl group, a cholesteryl group, and a pyrenyl group. In particular, a cholesteryl group is preferred.

The unsaturated long-chain aliphatic group is preferably an aliphatic group having an unsaturated bond in its main chain, and having a chain structure as the main chain.

The unsaturated bond may be a double bond-type or a triple bond-type unsaturated bond. In particular, a double bond is preferred. The number of unsaturated bonds only has to be at least one, and is not limited. Alternatively, both the double bond and the triple bond may be included. It is preferred that one double bond be included.

The double bond may be a cis double bond or a trans double bond. In particular, a cis double bond is preferred.

The unsaturated long-chain aliphatic group is preferably a hexadecenyl group, an octadecenyl group, an octadecadienyl group, an octadecatrienyl group, an icosatrienyl group, an icosatetraenyl group, an octadecatrienyl group, an icosapentaenyl group, or a docosahexaenyl group.

The unsaturated long-chain aliphatic group is more preferably a 9-hexadecenyl group, a 9-octadecenyl group (oleyl group), a 12-octadecadienyl group, a 6,9,12-octadecatrienyl group, an 8,11,14-icosatrienyl group, a 5,8,11,14-icosatetraenyl group, a 9,12,15-octadecatrienyl group, a 5,8,11,14,17-icosapentaenyl group, or a 4,7,13,16,19-docosahexaenyl group.

The unsaturated long-chain aliphatic group is still more preferably a 9-octadecenyl group (oleyl group). For example, when $R^1$ represents a 9-octadecenyl group (oleyl group), examples of $R^2$ include an octadecyl group and a 9-octadecenyl group (oleyl group).

A preferred example of the unsaturated long-chain aliphatic group may further have at least one carbon atom substituted by a hetero atom in the group having the structure as exemplified above as a preferred example.

A preferred example of the unsaturated long-chain aliphatic group may further have the structure as exemplified above as a structure specific to an oxygen-containing hydrocarbon group, a nitrogen-containing hydrocarbon group, or a sulfur-containing hydrocarbon group, based on the group having the structure as exemplified above as a preferred example.

A preferred example of the unsaturated long-chain aliphatic group may further have at least one substituent in the group having the structure as exemplified above as a preferred example. The substituent preferably shows hydrophobicity. Examples of the substituent include a phenyl group, a cholesteryl group, and a pyrenyl group. In particular, a cholesteryl group is preferred.

3. Description of Production Method

The polyamidoamine dendron of the present invention can be produced, for example, as described below.

[Chem. 1]

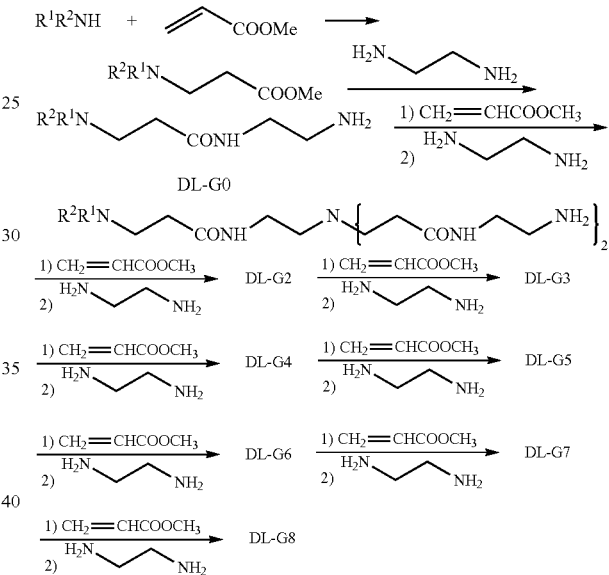

4. Description of Preferred Polyamidoamine Dendron

A preferred polyamidoamine dendron of the present invention is described below.

[Chem. 2]

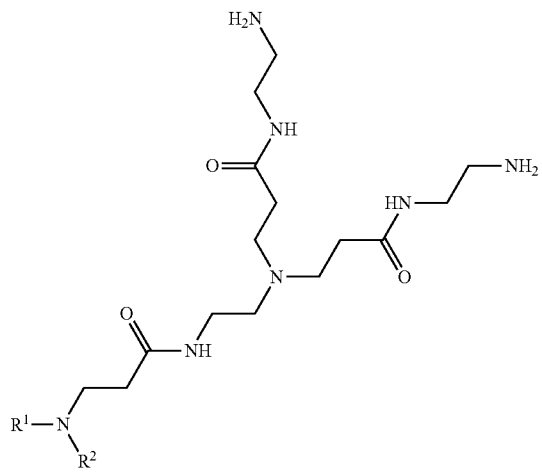

DL-G1

DL-G2
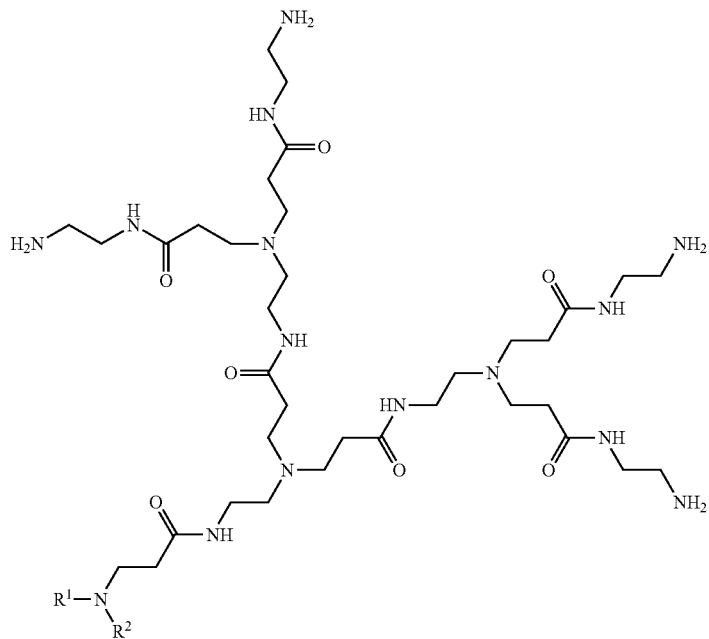
DL-G3
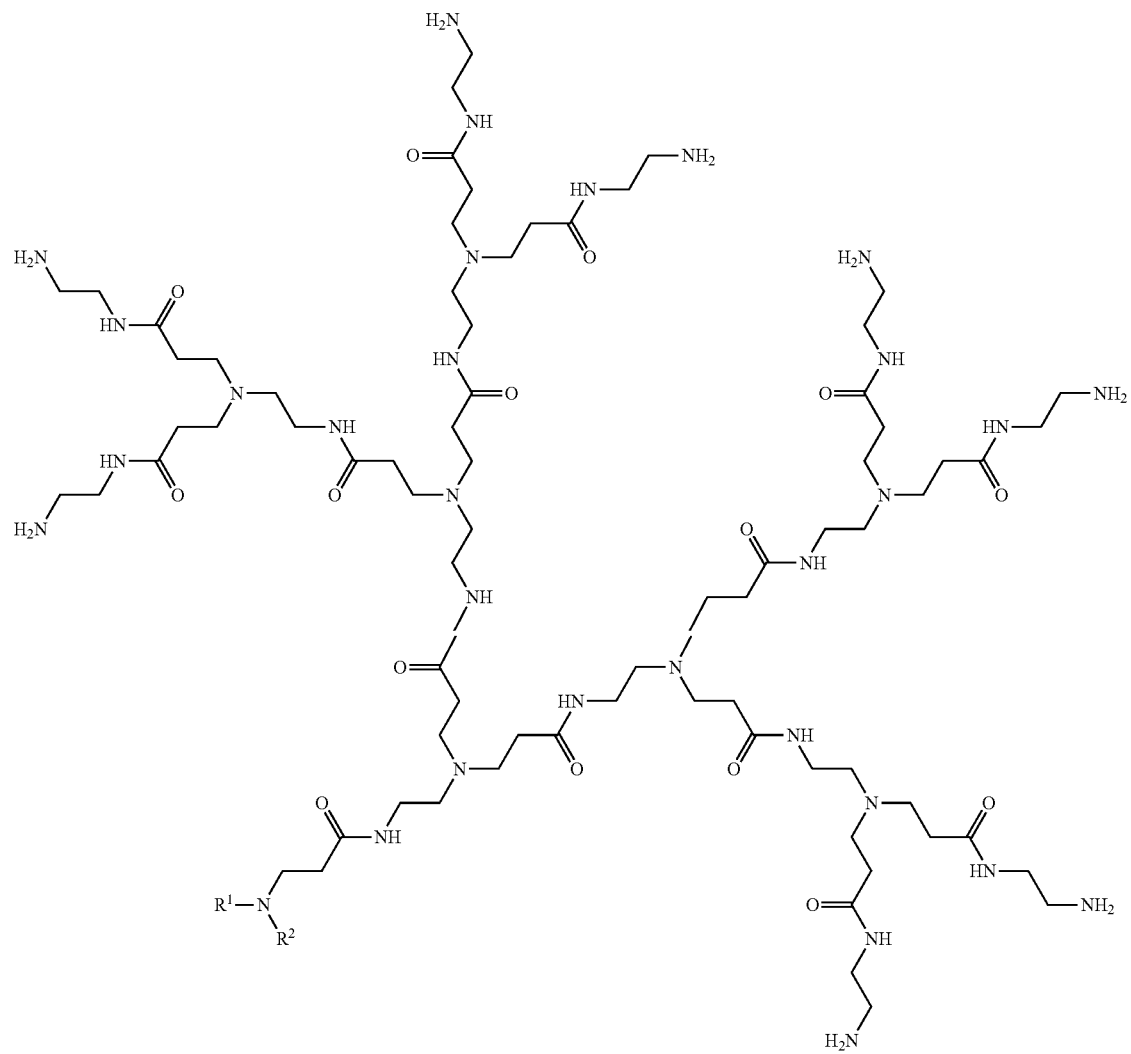

DL-G4
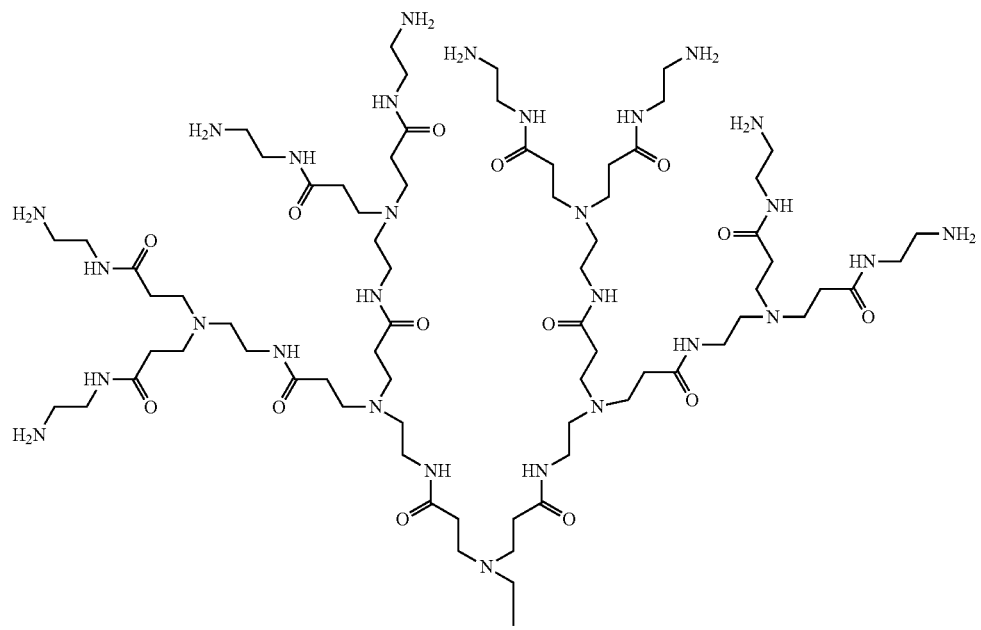
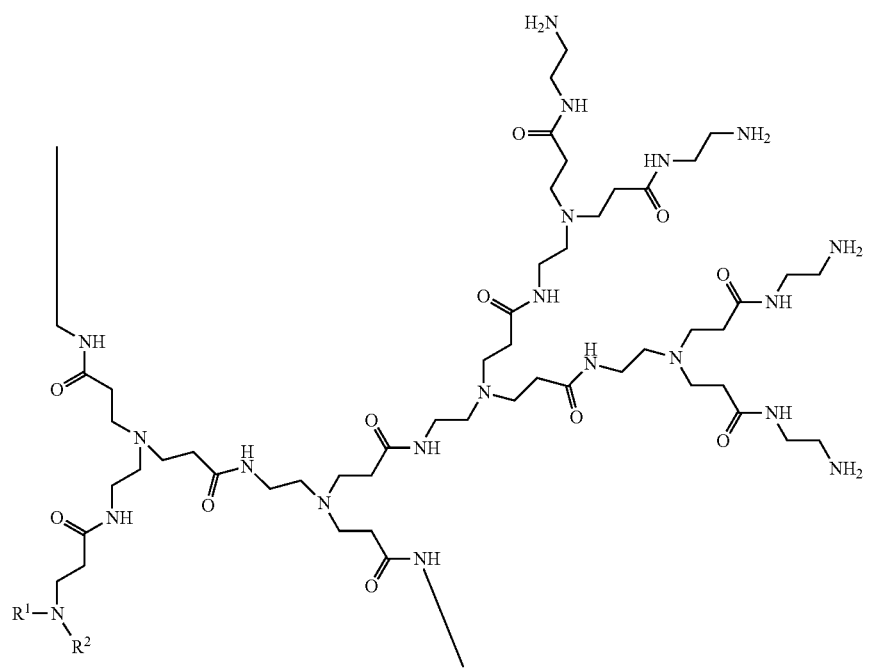

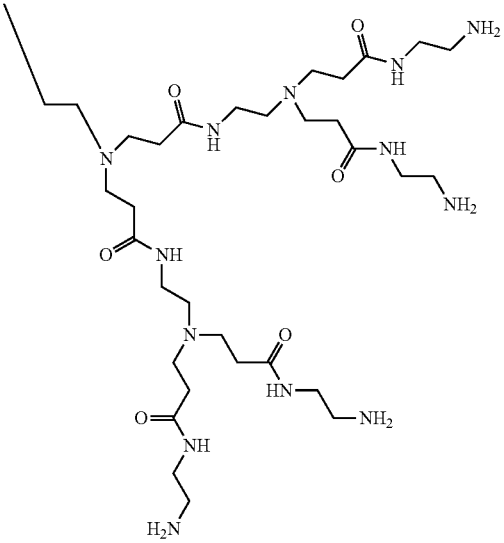

5. Other Descriptions

The gene transfer agent composition of the present invention may suitably include a phospholipid, in addition to the polyamidoamine dendron. Examples of such phospholipids include phosphatidylethanolamine, phosphatidylcholine, phosphatidylserine, phosphatidylinositol, phosphatidylglycerol, cardiolipin, sphingomyelin, plasmalogen, and phosphatidic acid. These phospholipids may be used singularly, or in a combination of two or more. Of these, phosphatidylethanolamine and phosphatidylcholine are preferably used singularly, or in combination. The fatty acid residue in these phospholipids is not particularly limited, and examples thereof include a saturated or unsaturated fatty acid residue having 12 to 18 carbon atoms. Specific examples thereof include a lauroyl group, a myristoyl group, a palmitoyl group, a stearoyl group, an oleoyl group, and a linoleyl group. In particular, dioleoylphosphatidylethanolamine (DOPE) is preferred.

The blending amount of the phospholipid is not particularly limited. The blending amounts of the phospholipid and the polyamidoamine dendron are 30 to 90 parts by weight and 70 to 10 parts by weight, preferably 50 to 80 parts by weight and 50 to 20 parts by weight, more preferably 60 to 70 parts by weight and 40 to 30 parts by weight, respectively, with respect to 100 parts by weight of the total amount of the phospholipid and the polyamidoamine dendron.

In addition to the phospholipid, cholesterol is an exemplary additive that may be contained in the gene transfer agent composition.

In the case of using the polyamidoamine dendron alone, the blending ratio of the gene and gene transfer agent is 1 to 20 parts by weight, preferably 3 to 15 parts by weight, more preferably 5 to 7 parts by weight of the gene transfer agent with respect to 1 part by weight of the gene. In addition, in the case of using a mixture of the polyamidoamine dendron and the phosphatide, the blending ratio of the gene and the gene transfer agent is 1 to 50 parts by weight, preferably 5 to 30 parts by weight, more preferably 10 to 15 parts by weight of the gene transfer agent with respect to 1 part by weight of the gene.

The gene may be any of an oligonucleotide, DNA, or RNA. In particular, preferred are a gene for in vitro transfer such as transformation; and a gene that exhibits an action through its in vivo expression, such as a gene for gene therapy and a gene used for the breeding of experimental animals and industrial animals such as domestic animals. Examples of the gene for gene therapy include genes encoding an antisense oligonucleotide, antisense DNA, antisense RNA, enzyme, or a biologically active substance such as a cytokine.

Cells into which the gene is transferred may include eukaryotic cells such as animal cells (e.g., human cells), and plant cells and prokaryotic cells such as bacterial cells.

As forms of the composition of the present invention, the polyamideamine dendron (DL-G1 to DL-G4) may be present singularly, the polyamidoamine dendron and the phospholipid may be present as a mixture, or the polyamidoamine dendron and the phospholipid may be combined to form a lipid membrane structure. The form of the lipid membrane structure and the production method therefor are not particularly limited. However, examples of the form include a form of a dried lipid mixture; a form dispersed in an aqueous solvent, and a dried form or frozen form thereof.

The dried lipid mixture can be produced by, for example, once dissolving a lipid component to be used in an organic solvent such as chloroform; and then evaporating the solution to dryness under reduced pressure with an evaporator, or spray-drying the solution with a spray drier.

Examples of the form of the lipid membrane structure dispersed in an aqueous solvent include a unilamellar liposome, a multilamellar liposome, an O/W emulsion, a W/O/W emulsion, a spherical micelle, a worm-like micelle, and a layered structure having an irregular shape. The size of the lipid membrane structure in a dispersed state is not particularly limited. However, the particle size is, for example, 50 nm to several μm in the case of the liposome or the emulsion, and the particle size is 5 nm to 50 nm in the case of the spherical micelle. In the case of the worm-like micelle or the layered structure having an irregular shape, layers may be considered to be formed so that the thickness of each of the layers has a thickness of 5 nm to 10 nm.

The composition of the aqueous solvent (dispersion medium) is also not particularly limited. However, examples of the aqueous solvent include: water; an aqueous solution of a sugar such as glucose, lactose, or sucrose; an aqueous solution of a polyhydric alcohol such as glycerin or propylene glycol; a buffer such as a phosphate buffer, a citrate buffer, or a phosphate buffered saline; physiological saline; and a medium for cell culture. In order to stably preserve the lipid membrane structure dispersed in the aqueous solvent for a long period of time, it is important, from the viewpoint of physical stability issues such as aggregation, to eliminate as many electrolytes from the aqueous solvent as possible. Further, it is important, from the viewpoint of chemical stability of the lipid, to set the pH of the aqueous solvent in the range of slightly acidic to almost neutral (pH 3.0 to 8.0), and to remove dissolved oxygen by nitrogen-bubbling. Additionally, effective preservation can be achieved by using the aqueous solution of a sugar in the case of performing freeze-drying preservation or spray-drying preservation, and by using the aqueous solution of a sugar and the aqueous solution of a polyhydric alcohol in the case of performing freeze preservation.

The concentration of such an additive in the aqueous solvent is not particularly limited. However, in the aqueous solution of a sugar, the concentration of the sugar is, for example, preferably 2 to 20% (W/V), more preferably 5 to 10% (W/V). Further, in the aqueous solution of a polyhydric alcohol, the concentration of the polyhydric alcohol is preferably 1 to 5% (W/V), more preferably 2 to 2.5% (W/V). In the buffer, the concentration of a buffering agent is preferably 5 to 50 mM, more preferably 10 to 20 mM.

The concentration of the lipid membrane structure in the aqueous solvent is not particularly limited. In the present invention, however, the concentration of the total amount of the phospholipid used as the lipid membrane structure is preferably 0.001 mM to 100 mM, more preferably 0.01 mM to 20 mM.

The form of the lipid membrane structure being dispersed in the aqueous solvent can be produced by adding the above-mentioned dried lipid mixture to the aqueous solvent, and emulsifying the mixture with an emulsifier such as a homogenizer, an ultrasonic emulsifier, a high pressure jet emulsifier, or the like. Alternatively, the form may be produced by a method well known as a production method for a liposome, such as a reversed phase evaporation method, without any particular limitation. When control is sought over the size of the lipid membrane structure, extrusion (extrusion filtration) may be performed under high pressure using a membrane filter with a uniform pore size, or the like.

Additionally, examples of the method of further drying the lipid membrane structure dispersed in the above-mentioned aqueous solvent may include normal freeze-drying or spray-drying. As the aqueous solvent used in this case, as described above, an aqueous solution of a sugar, preferably an aqueous solution of sucrose or an aqueous solution of lactose, may be used. Here, when the lipid membrane structure dispersed in the aqueous solvent is once produced and further dried, the long-term preservation of the lipid membrane structure becomes possible. Additionally, when an aqueous solution of a gene is added to the dried lipid membrane structure, the lipid mixture is hydrated efficiently. Thus, there is an advantage in that the gene itself can be efficiently retained in the lipid membrane structure.

The gene transfer agent of the present invention is applicable not only to a gene, but also to drugs that have difficulty transferring into cells, such as drugs having high hydrophilicity, high-molecular-weight biologically active peptides, or proteins. The use of the composition of the present invention allows the gene to be efficiently transferred into cells in vitro and in vivo.

The in vitro gene transfer may be performed by means such as addition of the gene-containing transfer agent composition of the present invention to a suspension containing target cells, or culture of target cells in a medium containing the gene-containing composition of the present invention.

The in vivo gene transfer may be performed by administrating the gene-containing composition of the present invention to a host. Means for administrating the composition to the host may be oral administration or parenteral administration. In particular, parenteral administration is preferred. As a dosage form, any of the commonly known dosage forms may be used. Examples of the dosage form for oral administration include a tablet, a powder, a granule, and a syrup. Further, examples of the dosage form for parenteral administration include an injection, an ophthalmic solution, an ointment, and a suppository. Of these, an injection is preferred. A preferred administration method is intravenous injection or local administration to target cells or a target organ.

EXAMPLES

Hereinafter, the present invention is described in further detail by way of examples. However, the present invention is not limited to only the following examples.

It should be noted that, in the following examples, the term "lipoplex" means a complex of the polyamidoamine dendron of the present invention and DNA.

Example 1

Synthesis of Gene Transfer Agent Composition of Present Invention

1. Synthesis of Polyamidoamine Dendron
(1) Synthesis of Oleyloleoylamide 7.78 ml ($20.0 \times 10^{-3}$ mol) of oleoyl chloride was dissolved in 100 ml of dichloromethane, and $N_2$ gas replacement was sufficiently performed. The reaction vessel was cooled in an ice water bath, and stirred. To the stirred solution, a solution obtained by dissolving 9.40 ml ($20.0 \times 10^{-3}$ mol) of oleylamine and 3.3 ml (0.024 mol) of triethylamine in 50 ml of dichloromethane was gradually added dropwise using a dropping funnel. Then, the mixture was stirred for 70 hours at room temperature while introducing $N_2$ gas. After completion of the reaction, the solvent was distilled off using a rotary evaporator. The resulting crude product was separated and purified by open column chromatography (eluent: chloroform/ethyl acetate=2/1; filler: silica gel). The resulting crude crystal was recrystallized using ethanol at −20° C. The product obtained as a white solid was dried at normal temperature under reduced pressure.

Figure 1:
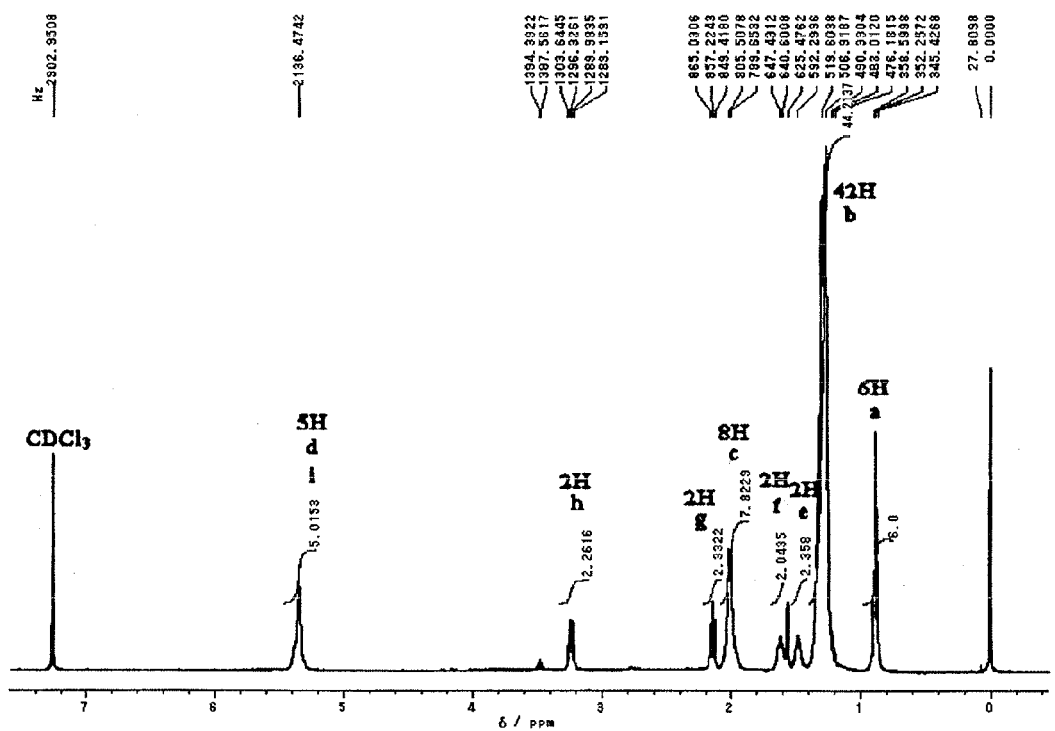
FIG. 1 is a $^1$H NMR spectrum (400 MHz, CDCl$_3$) showing that oleyloleoylamide is generated.
Figure 1:
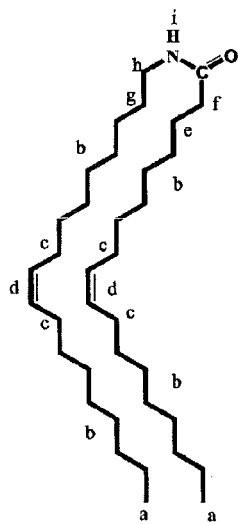

FIG. 1 shows a $^1$H NMR spectrum (400 MHz, CDCl$_3$) of the product. The yield of the product was 7.53 g (70.7%).

The product was oleyloleoylamide (Chem. 3).

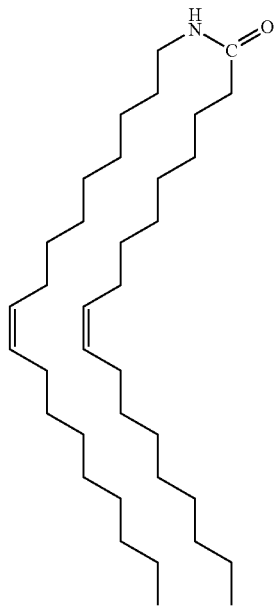

[Chem. 3]

(2) Synthesis of Dioleylamine 2.84 g (5.33×10$^{-3}$ mol) of oleyloleoylamide (Chem. 4) was dissolved in 80 ml of tetrahydrofuran (THF). The resulting solution was gradually added dropwise using a dropping funnel to a suspension was prepared by gradually adding 1.40 g (37.0×10$^{-3}$ mol) of lithium aluminum hydride (LAH) to 80 ml of THF. Then, the mixture was stirred for 8 days at 50° C. After completion of the reaction, LAH separated by suction filtration was washed once with THF, twice with chloroform, and once with ethanol. The LAH was separated by filtration again, and the solvent was distilled off using a rotary evaporator. Then, the resultant was washed three times with brine, and dried using sodium sulfate. The resulting crude product was separated and purified by open column chromatography (eluent: chloroform/ethyl acetate=2/1, and then chloroform/methanol=9/1; filler: silica gel). The product obtained as a yellow, oily substance was dried at normal temperature under reduced pressure.

Figure 2:
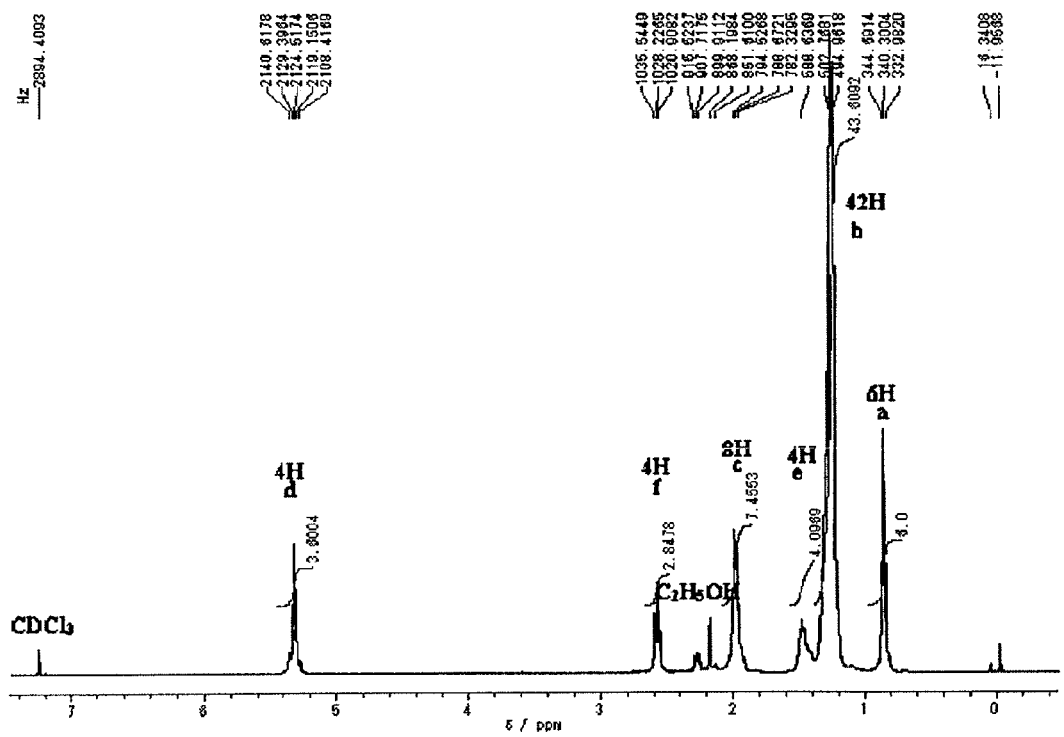
FIG. 2 is a $^1$H NMR spectrum (400 MHz, CDCl$_3$) showing that dioleylamine is generated.
Figure 2:
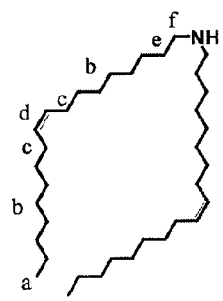

FIG. 2 shows a $^1$H NMR spectrum (400 MHz, CDCl$_3$) of the product. The yield of the product was 1.59 g (58.2%).

The product was dioleylamine (Chem. 4).

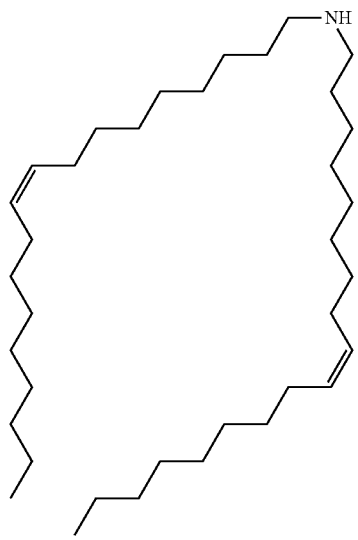

[Chem. 4]

(3) Additional synthesis of DL-G-0.5-2C18-U2

1.59 g (3.07×10$^{-3}$ mol) of dioleylamine was dissolved in 28 ml (0.31 mol) of methyl acrylate, and the solution was stirred at 70° C. while introducing N$_2$ gas. Because TLC indicated that the reaction did not proceed significantly, 14 ml of methyl acrylate was added 48 hours and 136 hours after initiation of the reaction (56 ml in total). After completion of the reaction (168 hours), unreacted methyl acrylate was distilled off using a rotary evaporator. The resulting crude product was separated and purified by open column chromatography (eluent: chloroform/ethyl acetate=2/1; filler: silica gel). The product obtained as a yellow, oily substance was dried at normal temperature under reduced pressure.

Figure 3:
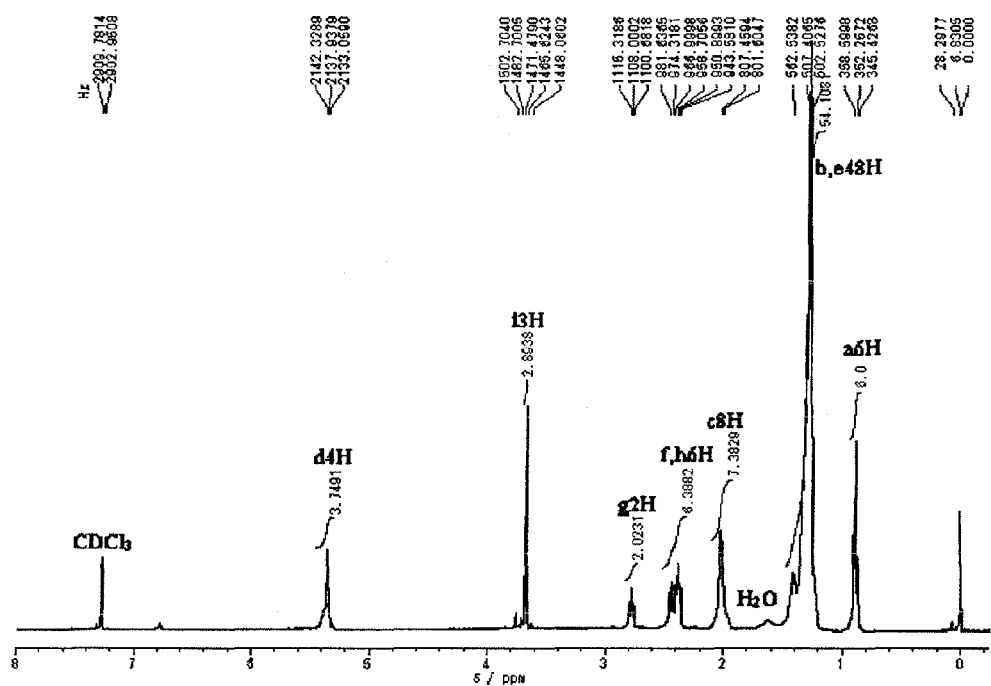
FIG. 3 is a $^1$H NMR spectrum (400 MHz, CDCl$_3$) showing that DL-G-0.5-2C18-U2 is generated.

FIG. 3 shows a $^1$H NMR spectrum (400 MHz, CDCl$_3$) of the product. The yield of the product was 1.42 g (76.6%).

The product (Chem. 5) was named DL-G-0.5-2C18-U2.

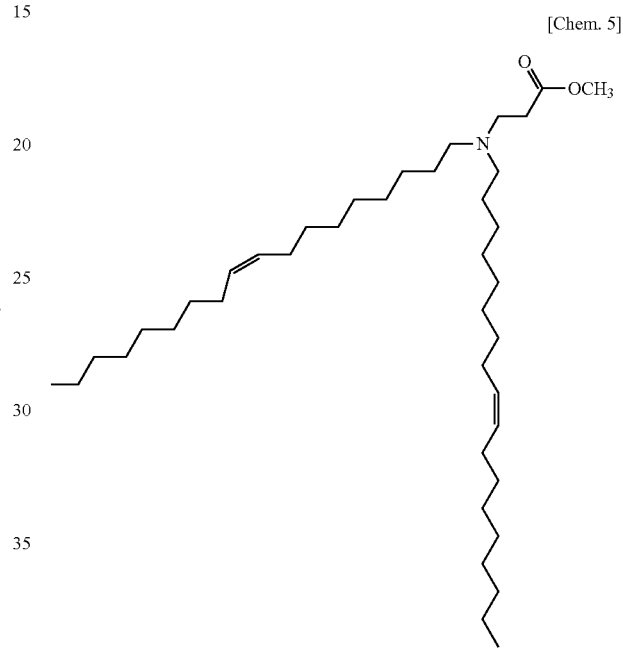

[Chem. 5]

(4) Synthesis of DL-G0-2C18-U2

1.42 g (2.35×10$^{-3}$ mol) of DL-G-0.5-2C18-U2 was dissolved with heat in 100 ml of methanol. The solution was gradually added dropwise using a Pasteur pipette to 70 ml (1.05 mol) of ethylenediamine purified by distillation and containing 25.4 mg (0.52×10$^{-3}$ mol) of sodium cyanide. Then, the mixture was stirred at 70° C. for 7 days while introducing N$_2$ gas. After completion of the reaction, the solvent and unreacted ethylenediamine were distilled off using a rotary evaporator. The resulting crude product was separated and purified by open column chromatography (eluent: chloroform/methanol/water=60/35/5; filler: silica gel). The product obtained as a yellow, pasty substance was dried at normal temperature under reduced pressure.

Figure 4:
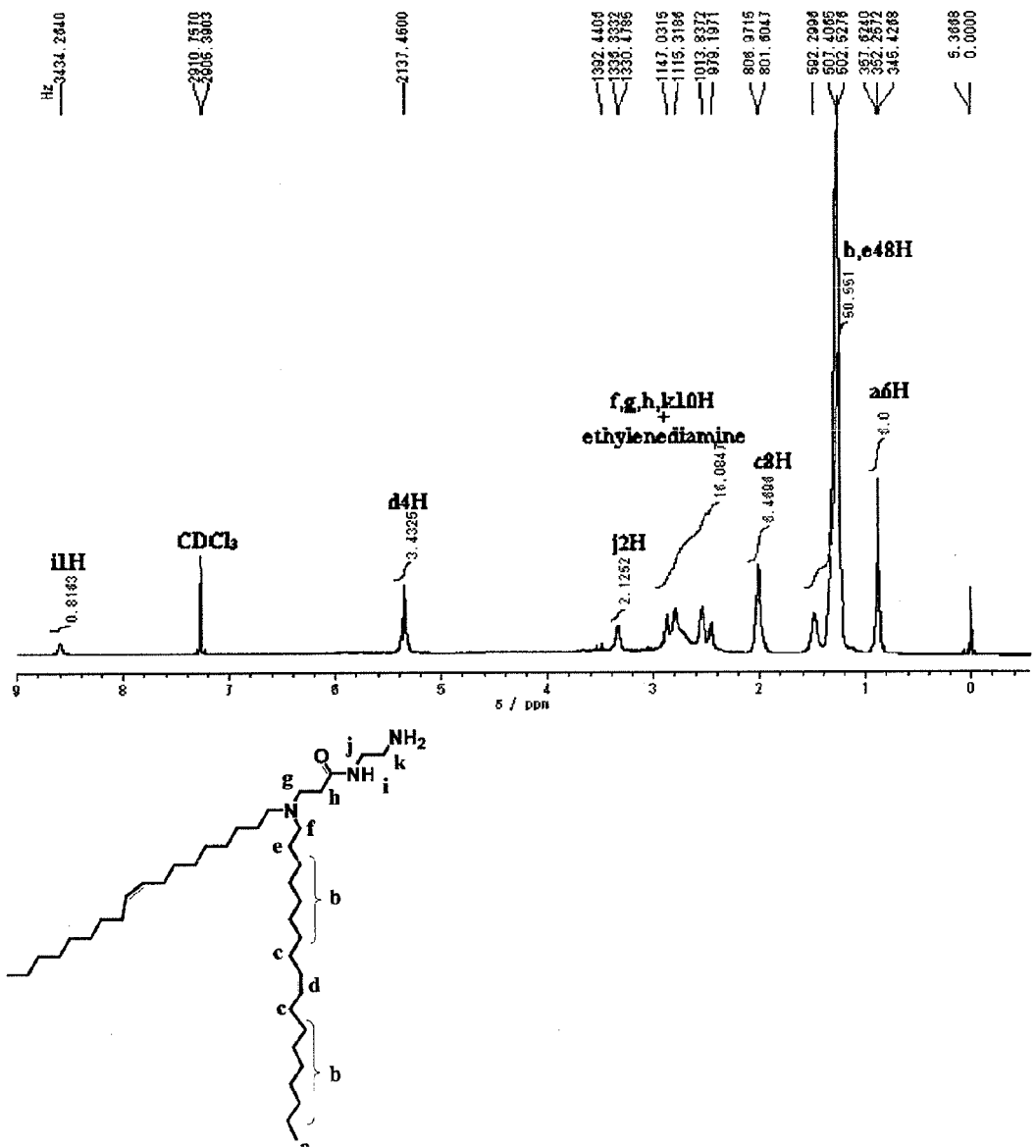
FIG. 4 is a $^1$H NMR spectrum (400 MHz, CDCl$_3$) showing that DL-G0-2C18-U2 is generated.

FIG. 4 shows a $^1$H NMR spectrum (400 MHz, CDCl$_3$) of the product. The yield of the product was 0.45 g (30.3%).

The product (Chem. 6) was named DL-G0-2C18-U2.

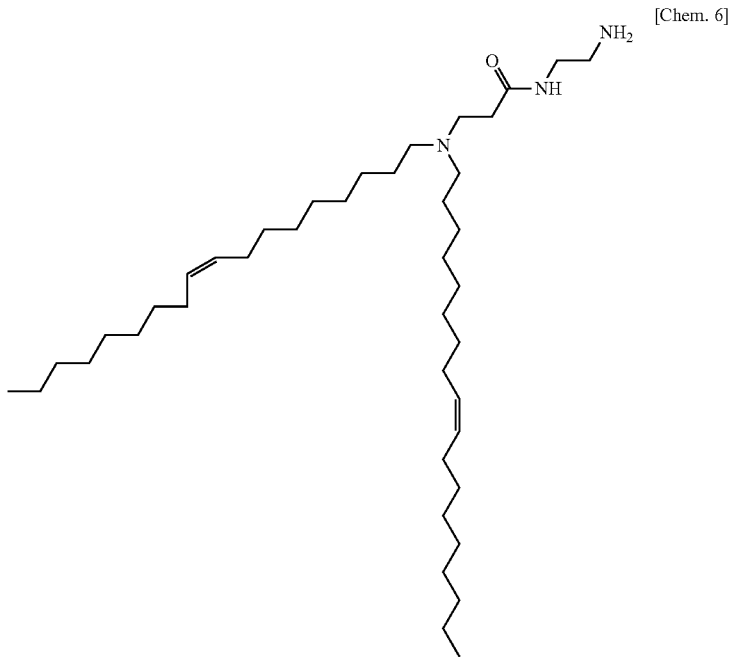 [SMILES: CCCCCCCC/C=C\CCCCCCCCN(CCCCCCCC/C=C\CCCCCCCC)CCC(=O)NCCN]

(5) Synthesis of DL-G0.5-2C18-U2

0.45 g ($0.71 \times 10^{-1}$ mol) of DL-G0-2C18 was dissolved with heat in 45 ml of methanol. The solution was gradually added dropwise using a Pasteur pipette to 30 ml (0.33 mol) of methyl acrylate. Then, the mixture was refluxed at 45° C. for 48 hours while introducing $N_2$ gas. After completion of the reaction, the solvent and unreacted methyl acrylate were distilled off using a rotary evaporator. The resulting crude product was separated and purified by open column chromatography (eluent: petroleum ether/ethyl acetate=10/3, and then chloroform/methanol=4/1; filler: silica gel). The product obtained as a yellow, oily substance was dried at normal temperature under reduced pressure.

Figure 5:
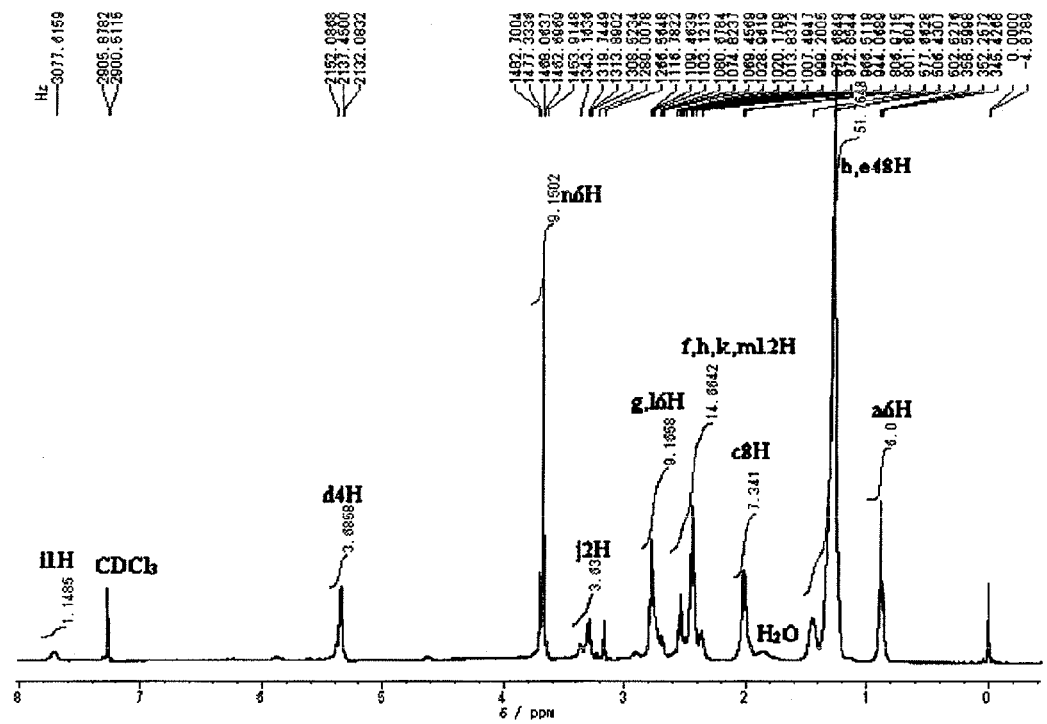
FIG. 5 is a $^1$H NMR spectrum (400 MHz, CDCl$_3$) showing that DL-G0.5-2C18-U2 is generated.
Figure 5:
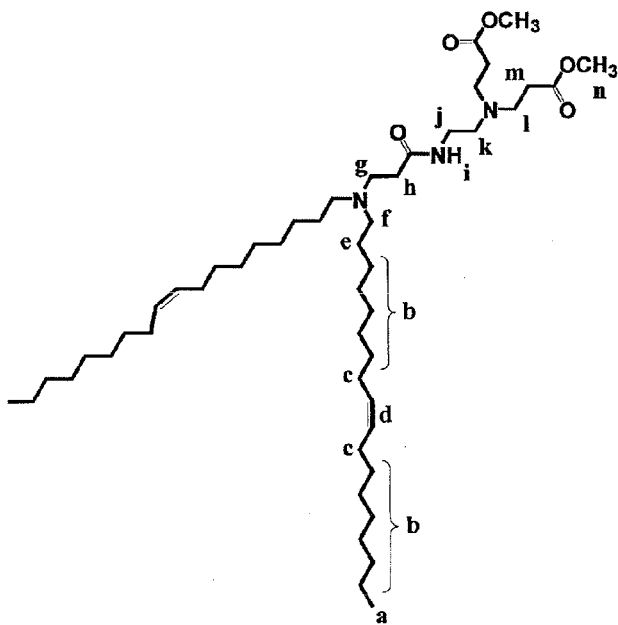

FIG. 5 shows a $^1$H NMR spectrum (400 MHz, $CDCl_3$) of the product. The yield of the product was 0.45 g (78.8%).

The product (Chem. 7) was named DL-G0.5-2C18-U2.

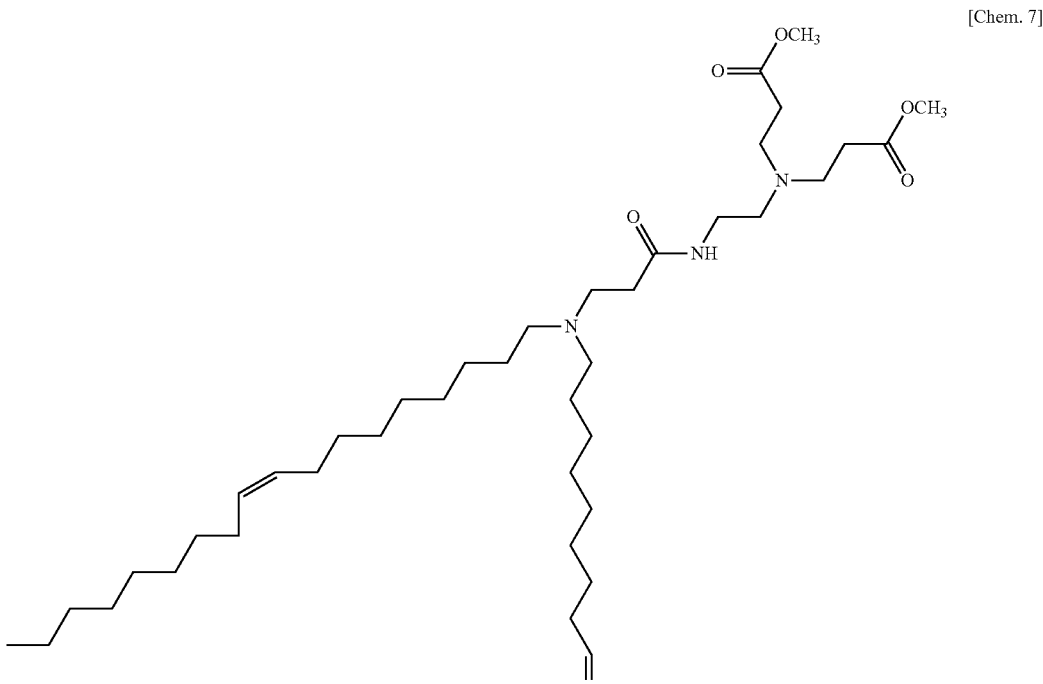

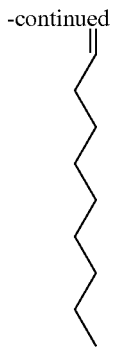

(6) Synthesis of DL-G1-2C18-U2

0.45 g ($0.56 \times 10^{-3}$ mol) of DL-G0.5-2C18 was dissolved with heat in 13 ml of methanol. The solution was gradually added dropwise using a Pasteur pipette to 24 ml (0.36 mol) of ethylenediamine purified by distillation and containing 12.0 mg ($0.25 \times 10^{-3}$ mol) of sodium cyanide. Then, the mixture was stirred at 50° C. for 45 hours while introducing $N_2$ gas. After completion of the reaction, the solvent and unreacted ethylenediamine were distilled off using a rotary evaporator. The product obtained as a yellow solid was dried at normal temperature under reduced pressure. The dried product was protonated with hydrochloric acid, dissolved in distilled water, then dialyzed for 3 days to remove unreacted ethylenediamine and the like; and then freeze-dried to give a yellow, powdery solid.

Figure 6:
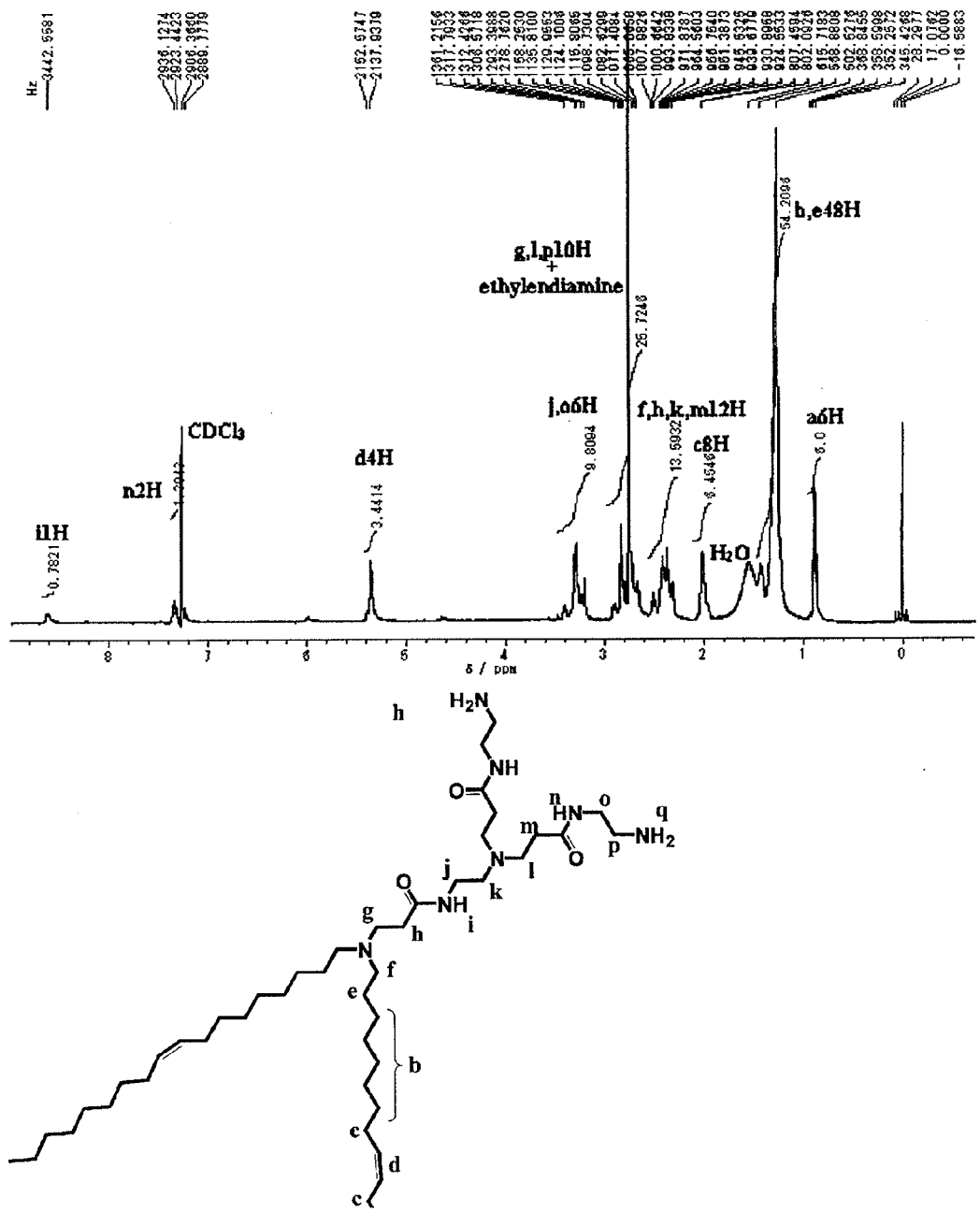
FIG. 6 is a $^1$H NMR spectrum (400 MHz, CDCl$_3$) showing that DL-G1-2C18-U2 is generated.

FIG. 6 shows a $^1$H NMR spectrum (400 MHz, $CDCl_3$) of the product. The yield of the product was 0.29 g (60.2%).

The product (Chem. 8) was named DL-G1-2C18-U2.

2. Preparation of Lipoplex (1) Preparation of Lipoplex of Polyamidoamine Dendron and Plasmid DNA A solvent was removed using a rotary evaporator from a chloroform solution of DL-G1-2C18-U2 obtained in Example 1 to form a lipid thin film. PBS was added to the lipid thin film, and the mixture was sonicated for 2 minutes using a bath-type ultrasonicator, thereby preparing a lipid dispersion liquid. Next, a solution of plasmid DNA (1 μg/50 μl) in 20 mM Tris-HCl and each of the lipid dispersion liquids (50 μl) having various concentrations were added and mixed; and then incubated at room temperature for 10 minutes, thereby obtaining a lipoplex.

(2) Preparation of lipoplex formed of DL-G1-2C18-U2, DOPE, and plasmid

To each of the mixed thin films formed of DL-G1-2C18-U2 and various amounts of DOPE, 0.5 ml of PBS was added; and

[Chem. 8]

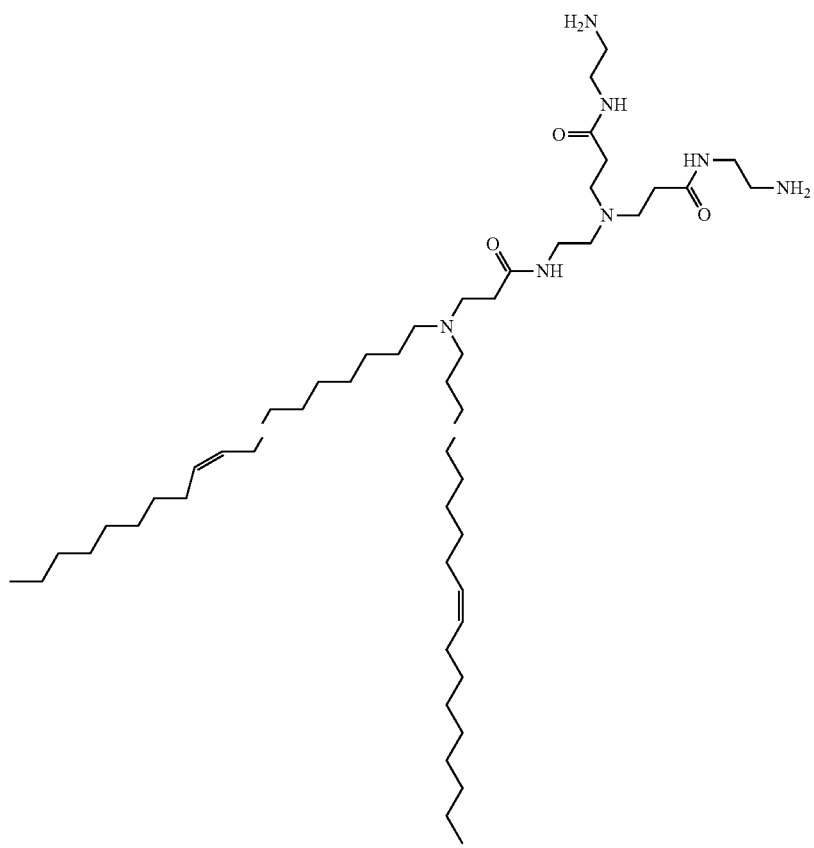

the mixture was sonicated for 2 minutes using a bath-type ultrasonicator, thereby preparing a mixed lipid dispersion liquid. The mixed lipid dispersion liquid was mixed with a solution of plasmid DNA (1 μg/50 μl) in 20 mM Tris-HCl at various N/P (primary amino group of DL-G1-2C18-U2/phosphate ester of DNA, mol/mol) ratios. The mixture was incubated at room temperature for 10 minutes to prepare a lipoplex.

Comparative Example 1

Synthesis of Gene Transfer Agent in which both of $R^1$ and $R^2$ of Polyamidoamine Dendron Represent Saturated Alkyl Group DL-G1-2C18 was synthesized as described below.
(1) Synthesis of DL-G-0.5-2C18
Dioctadecylamine (2.0 g, 3.8 mmol) was dissolved in methyl acrylate (35 ml, 0.39 mol) (dissolved with heating to 60 to 70° C.), and refluxed (80° C.) under a nitrogen atmosphere. After 18 hours, unreacted methyl acrylate was distilled off under reduced pressure using an evaporator. The residue was purified with silica (eluent: petroleum ether/diethyl ether=2/1). The yield of the product was 2.0 g (87.9%).

(2) Synthesis of DL-G0-2C18
DL-G-0.5 (2.0 g, 3.4 mmol) was dissolved in methanol (40 ml) (dissolved with heating). The solution was added dropwise to ethylenediamine (70 ml, 1.05 mol) purified by distillation containing sodium cyanide (33 mg, 0.67 mmol), and the mixture was stirred at 50° C. for 7 days under a nitrogen atmosphere. Then, the mixture was purified using silica (eluent: chloroform/methanol/water=60/35/5). The yield of the product was 1.4 g (53.2%).

(3) Synthesis of DL-G0.5-2C18
DL-G-0 (1.2 g, 1.9 mmol) was dissolved in methanol (20 ml). The solution was added dropwise to methyl acrylate (34 ml, 0.38 mol), and the mixture was stirred at 35° C. for 50 hours under a nitrogen atmosphere. Then, the mixture was purified using silica (eluent: petroleum ether/diethyl ether 2/1, and then chloroform/methanol=9/1). The yield of the product was 1.5 g (97.7%).

(4) Synthesis of DL-G1-2C18
DL-G-0.5 (1.5 g, 1.8 mmol) was dissolved in methanol (50 ml). The solution was added dropwise to ethylenediamine (65 ml, 0.92 mol) purified by distillation and containing sodium cyanide (18 mg, 0.37 mmol), and the mixture was stirred at 45° C. for 60 hours under a nitrogen atmosphere. Then, the mixture was purified using LH-20 (eluent: chloroform). The yield of the product was 1.5 g (94.3%).

Example 2

Gene Transfer (1)

1. Method
(1) Gene Transfer
HeLa cells derived from human cervical cancer were seeded in a 24-well dish at $5.0 \times 10^4$ cells per well, and cultured overnight at 37° C. in 0.5 ml of a DMEM medium containing 10% FBS. Then, the cells were washed twice with PBS containing 0.36 mM $CaCl_2$ and 0.42 mM $MgCl_2$ (PBS (+)). Next, 0.5 ml of a DMEM medium containing 10% FBS was added, and the cells were supplemented with a lipoplex (100 μl) containing 1 μg of plasmid DNA per well and incubated at 37° C. for 4 hours. Afterward, the cells were washed three times with PBS (+) to remove the lipoplex not incorporated into the cells. Then, 1 ml of a DMEM medium containing 10% FBS was added, and the cells were cultured at 37° C. for 40 hours.

(2) Evaluation of Gene Transfer by Luciferase Assay
The cells treated with the lipoplex and cultured for 40 hours were washed twice with PBS (+), and further washed once with PBS (−). The cells were dissolved by addition of 50 μl of a cytolytic agent per well and centrifuged at 12,000 rpm for 2 minutes, and the supernatant was collected. The luciferase activity and the amount of protein in the resulting cell lysate were determined by luciferase assay and a Coomassie (Bradford) Protein Assay Kit (PIERCE). It should be noted that the luciferase assay was performed in the following manner. First, tricine (358 mg) and $(MgCO_3)_4Mg(OH)_2 \cdot 5H_2O$ (69.3 mg) were dissolved in distilled water; and $MgSO_4$ (32.1 mg), EDTA (3.7 mg), DTT (513.6 mg), CoA (20.7 mg), ATP (29.2 mg), NaCl (800 mg), KCl (20 mg), $Na_2HPO_4$ (60 mg), and $KH_2PO_4$ (19 mg) were further added and dissolved. Next, the total volume of the solution was adjusted to 99 ml. To the solution (9.9 ml) was added 47 mM luciferin (0.1 ml), and the mixture was used as a luminescent substrate liquid. The luminescent substrate solution (20 μl) was mixed with a luminescent substrate liquid (95 μl) including luciferin (13.5 μg) and a 5 mg/ml albumin solution (5 ml), and subjected to measurement for 20 seconds with a Lumat LB9507 luminometer (Berthold Japan Co., Ltd.) for an amount of luminescence.

Figure 7:
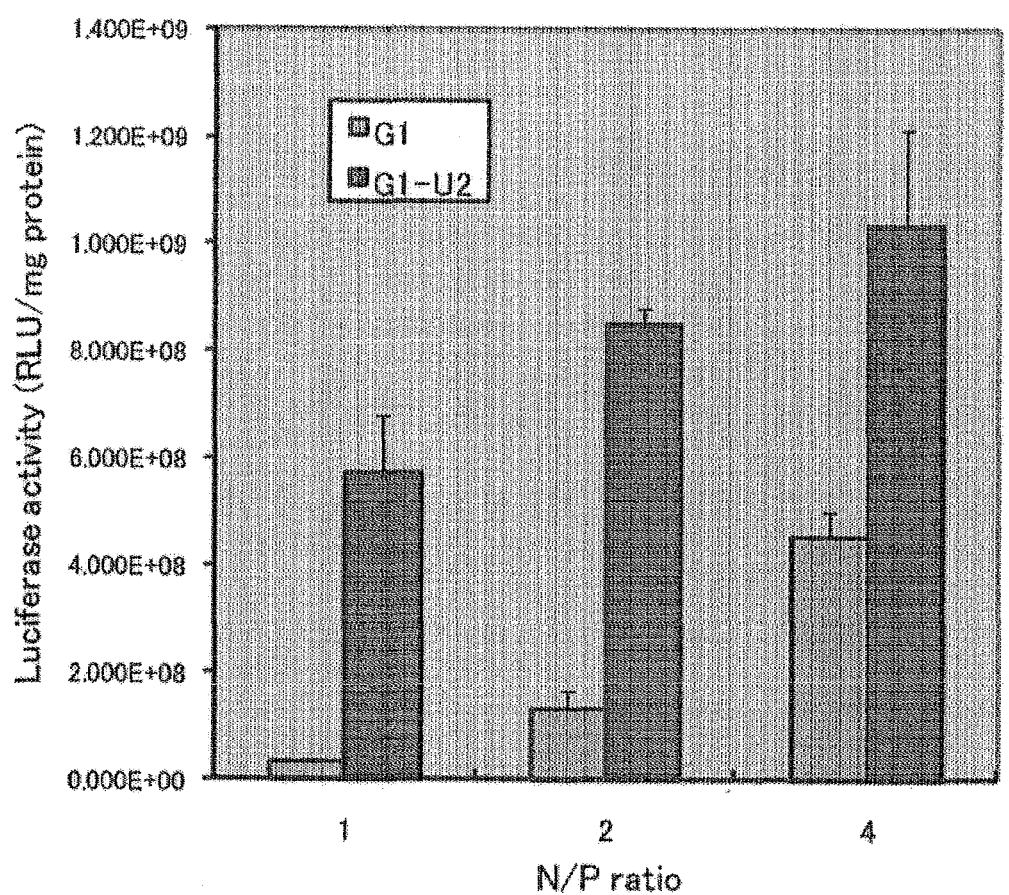
FIG. 7 is a graph showing luciferase activities (g of luciferase/mg of protein) of CV1 cells treated with DL-G1-

2. Results
As shown in FIG. 7 and FIG. 8, it is found that the gene transfer agent (G1-U2) of the present invention expresses extremely high gene transfer efficiency, two times higher than that of the gene transfer agent (G1) in which both of $R^1$ and $R^2$ of a polyamidoamine dendron represent saturated alkyl groups. The resulting gene transfer efficiency goes far beyond expectations.

Considering the reasons that the gene transfer efficiency goes far beyond expectations, one of the reasons is that an unsaturated alkyl chain is easily inserted into a cell membrane because of its high motility as compared to a saturated alkyl chain. However, this high gene transfer efficiency may be hardly described by only the mechanism of insertion into the cell membrane. Surprisingly, the high motility of the unsaturated alkyl group strongly induces membrane fusion by perturbing the cell membrane to enhance an interaction with an endosome membrane. It is expected that a gene may be transferred from an endosome to a cytosol through such a mechanism.

In addition, the unsaturated alkyl group having high motility is not expected to significantly impair the fluidity of the cell membrane, as compared to the saturated alkyl group. Thus, the gene transfer agent of the present invention using the unsaturated alkyl group also has an unexpected effect of reducing cytotoxicity more greatly.

Example 3

Gene Transfer (2)

DL-G1-2C18-U2 (DL-U2) in which both of $R^1$ and $R^2$ represent unsaturated alkyl groups, which was obtained in Example 1; and DL-G1-2C18 (DL-G1), in which both of $R^1$ and $R^2$ represent saturated alkyl groups, were compared as described below.

pEGFP-C1 expressing a green fluorescent protein was used as a gene transfer plasmid, and COS-7 cells were used as target cells. Lipoplexes were prepared using, individually, DL-U2 and DL-G1. Then, gene transfer was performed.

Specifically, the following procedures were employed.
1. Method
(1) Preparation of Lipoplex
Lipoplexes were prepared by the following procedures, using pEGFP-C1 as plasmid DNA expressing a green fluorescent protein.

A solvent was removed from each of chloroform solutions (1 mg/ml) of polyamidoamine dendrons (DL-G1 and DL-G1-U2) using a rotary evaporator to form 111.5 µg of lipid thin films. The thin films were dried in vacuo for 2 hours. Then, 500 µl of phosphate buffered saline (PBS) were added. The mixtures were further sonicated for 2 minutes using a bath-type ultrasonicator to give 160 µl of lipid dispersion liquids. In addition, a solution (20 µg/ml, 160 µl) prepared by dissolving plasmid DNA in a 20 mM Tris-HCl buffer was added to each of the lipid dispersion liquids so as to obtain different N/P ratios. Then, the liquids were incubated at room temperature for 30 minutes to obtain lipoplexes.

(2) Expression of GFP
Preceding Day
COS7 cells were seeded in a 24-well plate.
(COS7 cells: $2.0 \times 10^4$ cells/well·DMEM+10% FBS (Pe/St) 500 µl)
Expression Day
(i) To a 20 mM Tris-HCl (pH 7.4) buffer was added 2.0 µg of plasmid DNA (pCAG-GFP) so as to prepare a 2.0 µg/100 µl solution.
(ii) To 100 µl of the plasmid DNA solution prepared in step (i) was added 50 µl of a DL-G1 or DL-U2 liposome solution (N/P ratio=4), and the whole was thoroughly mixed using a vortex and incubated at room temperature for 30 minutes.
(iii) 50 µl of an Opti-MEM (registered trademark) I Reduced-Serum Medium was further added, and the whole was thoroughly mixed and allowed to stand at room temperature for 5 minutes.
(iv) 20, 50, or 100 µl per well of the DL-plasmid DNA complex solution was added, and the whole was mixed by shaking the plate so as to be homogeneous.
(v) The cells were incubated at 37° C. in 5% $CO_2$ for 4 hours, and the growth medium was replaced.
(vi) 48 hours later, GFP-expressing cells were observed with a fluorescence microscope (Olympus, CKX41) (observed at a magnification of 100×).

(3) Luciferase Activity Measurement
Preceding Day
COS7 cells were seeded in a 24-well plate.
(COS7 cells: $2.0 \times 10^4$ cells/well·DMEM+10% FBS (Pe/St) 500 µl)
Measurement Day
(i) A 20 mM Tris-HCl (pH 7.4) buffer was dispensed into three tubes at, individually, 363 µl (for NP ratio=2), 288 µl (for NP ratio=4), and 138 µl (for NP ratio=8).
(ii) 6.0 µg of plasmid DNA (pEGFP-luc+) was added to each of the three tubes prepared in step (i) at 12 µl (6.0 µg), and the contents were stirred.
(iii) A DL-G1 or DL-U2 liposome solution was added to the three tubes prepared in step (ii) at, individually, 75 µl (N/P ratio=2), 150 µl (N/P ratio=4), and 300 µl (N/P ratio=8).
(iv) 150 µl of an Opti-MEM (registered trademark) I Reduced-Serum Medium was further added, and the whole was thoroughly mixed and allowed to stand at room temperature for 5 minutes.
(v) 20, 50, and 100 µl per well of the DL-plasmid DNA complex solution was individually added to three wells, and the contents were mixed.
(vi) The cells were incubated at 37° C. in 5% $CO_2$ for 4 hours, and the growth medium was replaced.
(vii) 24 hours later, luciferase activity was measured according to the protocol of the luciferase assay system (Promega, E1501).

2. Results
The results are shown in FIGS. 9 (GFP expression) and 10 (luciferase activity measurement).

Example 4

Gene Transfer (3)

DL-U2, which was obtained in Example 1, and DL-G1 were compared as described below.
pEGFP-C1 expressing a green fluorescent protein was used as a gene transfer plasmid, and NHDF-ad cells were used as target cells. Lipoplexes were prepared using, individually, DL-U2 and DL-G1. Then, gene transfer was performed.
Specifically, the following procedures were employed.
The lipoplexes were prepared in the same manner as in Example 3.

1. Method
(1) Expression of GFP
Preceding Day
NHDF-ad cells were seeded in a 24-well plate.
(NHDF-ad cells: $2.5 \times 10^4$ cells/well·DMEM+10% FBS (Pe/St) 500 µl)
Expression Day
(i) A 20 mM Tris-HCl (pH 7.4) buffer was dispensed into two tubes at, individually, 56.3 µl (for NP ratio=3) and 37.5 µl (for NP ratio=6).
(ii) 1.0 µg of plasmid DNA (pCAG-GFP) was added to each of the two tubes prepared in step (i) at 2 µl (1.0 µg), and the contents were stirred.
(iii) To the prepared plasmid DNA solutions was added, individually, 18.7 µl of a DL-G1 liposome solution (N/P ratio=3) and 37.5 µl of a DL-U2 liposome solution (N/P ratio=6); and the contents were thoroughly mixed using a vortex, and incubated at room temperature for 30 minutes.
(iv) 25 µl of an Opti-MEM (registered trademark) I Reduced-Serum Medium was further added, and the whole was thoroughly mixed and allowed to stand at room temperature for 5 minutes.
(v) 50 µl per well of the DL-plasmid DNA complex solutions was added, and the whole was mixed by shaking the plate so as to be homogeneous.
(vi) The cells were incubated at 37° C. in 5% $CO_2$ for 4 hours, and the growth medium was replaced.
(vii) 48 hours later, GFP-expressing cells were observed with a fluorescence microscope (Olympus, CKX41) (observed at a magnification of 100×).

(2) Luciferase Activity Measurement
Preceding Day
NHDF-ad cells were seeded in a 24-well plate.
(NHDF-ad cells: $2.5 \times 10^4$ cells/well·DMEM+10% FBS (Pe/St) 500 µl)
Measurement Day
(i) A 20 mM Tris-HCl (pH 7.4) buffer was dispensed into three tubes at, individually, 363 µl (for NP ratio=2), 288 µl (for NP ratio=4), and 138 µl (for NP ratio=8).
(ii) 6.0 µg of plasmid DNA (pEGFP-luc+) was added to each of the three tubes prepared in step (i) at 12 µl (6.0 µg), and the contents were stirred.
(iii) A DL-G1 or DL-U2 liposome solution was added to the three tubes prepared in step (ii) at, individually, 75 µl (N/P ratio=2), 150 µl (N/P ratio=4), and 300 µl (N/P ratio=8).
(iv) 150 µl of an Opti-MEM (registered trademark) I Reduced-Serum Medium was further added, and the whole was thoroughly mixed and allowed to stand at room temperature for 5 minutes.
(v) 20, 50, and 100 µl per well of the DL-plasmid DNA complex solutions was added, individually, to three wells, and the contents were mixed.

(vi) The cells were incubated at 37° C. in 5% $CO_2$ for 4 hours, and the growth medium was replaced.

(vii) 48 hours later, luciferase activity was measured according to the protocol of the luciferase assay system (Promega, E1501).

2. Results

The results are shown in FIGS. 11 (GFP expression) and 12 (luciferase activity measurement).

In the case of using the conventional polyamidoamine dendron (DL-G1) having a saturated alkyl group (2C18), GFP expression was observed in 10 to 20% of the cells. In contrast, in the case of using the polyamidoamine dendron (DL-G1-U2) having an unsaturated-type alkyl group (dioleyl) of the present invention, GFP expression was observed in 70 to 80% of the cells. Further, the results of flow cytometry reveals that the fluorescence intensity of GFP expressed in the cells treated with DL-G1-U2 is about ten times higher than that of the conventional DL-G1. As is evident from these results, the unsaturated type polyamidoamine dendron of the present invention has a significantly high gene transfer activity as compared to the conventional saturated alkyl chain type polyamidoamine dendron.

It should be noted that NHDF-ad cells, which are normal epithelial cells derived from adult humans, are also used in the production of iPS cells. The use of the conventional saturated type polyamidoamine dendron did not allow a gene to be transferred into the NHDF-ad cells. In contrast, the use of the unsaturated type polyamidoamine dendron of the present invention allowed the gene to be transferred into the cells.

Example 5

Gene Transfer (4)

DL-U2, which was obtained in Example 1, and a commercially available gene transfer agent were compared, as described below.

pEGFP-C1 expressing a green fluorescent protein was used as a gene transfer plasmid; and adherent cells COS-7 and Hela-S3, and non-adherent cells K562, which were established cell lines, were used as target cells. Lipoplexes were individually prepared using DL-U2. Then, gene transfer was performed.

Specifically, the following procedures were employed.

The lipoplexes were prepared in the same manner as in Example 3.

1. Method (1) Expression of GFP

Preceding Day

COS7 cells and HeLa—S3 cells were seeded in a 24-well plate.

(COS7 cells: $2.0 \times 10^4$ cells/well·DMEM+10% FBS (Pe/St) 500 µl)

(HeLa—S3 cells: $3 \times 10^4$ cells/well·DMEM+10% FBS (Pe/St) 500 µl)

Expression Day

K562 cells were seeded in a 24-well plate.

($1 \times 10^5$ cells/well·RPMI1640+10% FBS (Pe/St) 500 µl)

(i) A 20 mM Tris-HCl (pH 7.4) buffer was dispensed into three tubes at 35.5 µl (for NP ratio=6) for each of two tubes, and 23 µl (for NP ratio=8) for the remaining tube.

(ii) 1.0 µg of plasmid DNA (pCAG-GFP) was added to each of the three tubes prepared in step (i) at 2 µl (1.0 µg), and the contents were stirred.

(iii) A DL-U2 liposome solution was added to the three tubes prepared in step (ii) at 37.5 µl (N/P ratio=6) for each of two tubes, and 50 µl (N/P ratio=8) for the remaining tube.

(iv) 25 µl of an Opti-MEM (registered trademark) I Reduced-Serum Medium was further added, and the whole was thoroughly mixed and allowed to stand at room temperature for 5 minutes.

(v) 100 µl of the DL-plasmid DNA complex solution (N/P ratio=6) was added and mixed with the COS7 cells.

100 µl of the DL-plasmid DNA complex solution (N/P ratio=6) was added and mixed with the HeLa—S3 cells.

50 µl of the DL-plasmid DNA complex solution (N/P ratio=8) was added and mixed with the K562 cells.

(vi) The cells were incubated at 37° C. in 5% $CO_2$ for 4 hours, and the growth medium was replaced (the medium was not replaced for the K562 cells).

(vii) 48 hours later, GFP-expressing cells were observed with a fluorescence microscope (Olympus, CKX41).

Lipofectamine LTX: Gene transfer was performed according to the protocol; and, 48 hours later, GFP-expressing cells were observed with a fluorescence microscope (Olympus, CKX41). DNA quantity COS7: 1.0 µg, HeLa—S3: 1.0 µg, K562: 0.5 µg FuGENE HD: Gene transfer was performed according to the protocol; and, 48 hours later, GFP-expressing cells were observed with a fluorescence microscope (Olympus, CKX41).

DNA quantity COS7: 1.0 µg, HeLa—S3: 1.0 µg, K562: 0.5 µg (2) Luciferase Activity Measurement Preceding Day COS7 cells and HeLa—S3 cells were seeded in a 24-well plate.

(COS7 cells: $2.0 \times 10^4$ cells/well·DMEM+10% FBS (Pe/St) 500 µl)

(HeLa—S3 cells: $3 \times 10^4$ cells/well·DMEM+10% FBS (Pe/St) 500 µl)

Measurement Day

K562 cells were seeded in a 24-well plate.

($1 \times 10^5$ cells/well·RPMI1640+10% FBS (Pe/St) 500 µl)

(i) A 20 mM Tris-HCl (pH 7.4) buffer was dispensed into each of three tubes at 144 µl (for NP ratio=4).

(ii) 3.0 µg of plasmid DNA (pEGFP-luc+) was added to each of the three tubes prepared in step (i) at 6 µl (3.0 µg), and the contents were stirred.

(iii) A DL-U2 liposome solution was added to each of the three tubes prepared in step (ii) at 75 µl (N/P ratio=4).

(iv) 75 µl of an Opti-MEM (registered trademark) I Reduced-Serum Medium was further added, and the whole was thoroughly mixed and allowed to stand at room temperature for 5 minutes.

(v) 50 µl of the DL-plasmid DNA complex solution was added to each of three wells containing the COS7 cells, and the contents were mixed.

50 µl of the DL-plasmid DNA complex solution was added to each of three wells containing the HeLa—S3 cells, and the contents were mixed.

100 µl of the DL-plasmid DNA complex solution was added to each of three wells containing the K562 cells, and the contents were mixed.

(vi) The cells were incubated at 37° C. in 5% $CO_2$ for 4 hours, and the growth medium was replaced (the medium was not replaced for the K562 cells).

(vii) 48 hours later, luciferase activity was measured according to the protocol of the luciferase assay system (Promega, E1501) (relative values based on the activity of LTX defined as 1 were graphed).

Lipofectamine LTX: Gene transfer was performed for three wells according to the protocol; and, 48 hours later, luciferase activity was measured according to the protocol of the luciferase assay system (Promega, E1501).

DNA quantity COS7: 0.2 μg, HeLa—S3: 0.2 μg, K562: 1.0 μg

FuGENE HD: Gene transfer was performed for three wells according to the protocol; and, 48 hours later, luciferase activity was measured according to the protocol of the luciferase assay system (Promega, E1501).

DNA quantity COS7: 0.5 μg, HeLa—S3: 0.5 μg, K562: 1.0 μg

2. Results

The results are shown in FIGS. 13 (GFP expression), 14 (luciferase activity measurement), and 15 (toxicity evaluation).

The gene transfer activity was compared between each of commercially available gene transfer agents Lipofectamine LTX and FuGENE HD, which are presently in frequent use, and the polyamidoamine dendron of the present invention. The polyamidoamine dendron of the present invention showed an excellent gene transfer activity and lower cytotoxicity on any of adherent cells (COS-7 and HeLa—S3) and non-adherent cells (K562).

Example 6

Gene Transfer (5)

DL-U2, which was obtained in Example 1, and a commercially available gene transfer agent were compared, as described below.

pEGFP-C1 expressing a green fluorescent protein was used as a gene transfer plasmid; and NHDF-ad cells, which were normal epithelial cells derived from adult humans and also used for the production of iPS cells, were used as target cells. Lipoplexes were individually prepared using DL-U2. Then, gene transfer was performed.

Specifically, the following procedures were employed.

The lipoplexes were prepared in the same manner as in Example 3.

1. Method (1) Expression of GFP

Preceding Day

NHDF-ad cells were seeded in a 24-well plate.
(NHDF-ad cells: 2.5×10$^4$ cells/well·DMEM+10% FBS (Pe/St) 500 μl)

Expression Day (i) A 20 mM Tris-HCl (pH 7.4) buffer was dispensed into two tubes at, individually, 56.3 μl (for NP ratio=3) and 37.5 μl (for NP ratio=6).
(ii) 1.0 μg of plasmid DNA (pCAG-GFP) was added to each of the two tubes prepared in step (i) at 2 μl (1.0 μg), and the contents were stirred.
(iii) To the prepared plasmid DNA solutions was individually added 18.7 μl of a DL-G1 liposome solution (N/P ratio=3) and 37.5 μl of a DL-U2 liposome solution (N/P ratio=6), and the contents were thoroughly mixed using a vortex and incubated at room temperature for 30 minutes.
(iv) 25 μl of an Opti-MEM(R) I Reduced-Serum Medium was further added, and the whole was thoroughly mixed and allowed to stand at, room temperature for 5 minutes.
(v) 50 μl per well of the DL-plasmid DNA complex solutions was added, and the whole was mixed by shaking the plate so as to be homogeneous.
(vi) The cells were incubated at 37° C. in 5% CO$_2$ for 4 hours, and the growth medium was replaced.
(vii) 48 hours later, GFP-expressing cells were observed with a fluorescence microscope (Olympus, CKX41) (observed at a magnification of 100×).

Lipofectamine LTX: Gene transfer was performed according to the protocol, and, 48 hours later, GFP-expressing cells were observed with a fluorescence microscope (Olympus, CKX41).
(observed at a magnification of 100×)
DNA quantity 0.2 μg FuGENE HD: Gene transfer was performed according to the protocol, and, 48 hours later, GFP-expressing cells were observed with a fluorescence microscope (Olympus, CKX41).
(observed at a magnification of 100×)
DNA quantity 0.2 μg FuGENE6: Gene transfer was performed according to the protocol, and, 48 hours later, GFP-expressing cells were observed with a fluorescence microscope (Olympus, CKX41).
(observed at a magnification of 100×)
DNA quantity 1.0 μg (2) Luciferase Activity Measurement Preceding Day NHDF-ad cells were seeded in a 24-well plate.
(NHDF-ad cells: 2.5×10$^4$ cells/well·DMEM+10% FBS (Pe/St) 500 μl)

Measurement Day (i) A 20 mM Tris-HCl (pH 7.4) buffer was dispensed into two tubes at 162.75 μl (for DL-G1) and 106.5 μl (for DL-U2), respectively.
(ii) 3.0 μg of plasmid DNA (pEGFP-luc+) were added to each of the two tubes prepared in step (i) at 6 μl (3.0 μg), and the contents were stirred.
(iii) To the prepared plasmid DNA solutions was added 112.5 μl of a DL-U2 liposome solution (N/P ratio=6), and the whole was thoroughly mixed using a vortex and incubated at room temperature for 30 minutes.
(iv) 75 μl of an Opti-MEM(R) I Reduced-Serum Medium was further added, and the whole was thoroughly mixed and allowed to stand at room temperature for 5 minutes.
(v) 20 and 50 μl per well of the DL-plasmid DNA complex solutions were individually added to three wells, and the contents were mixed.
(vi) The cells were incubated at 37° C. in 5% CO$_2$ for 4 hours, and the growth medium was replaced.
(vii) 48 hours later, luciferase activity was measured according to the protocol of the luciferase assay system (Promega, E1501).

Lipofectamine LTX: Gene transfer was performed according to the protocol, and luciferase activity was measured according to the protocol of the luciferase assay system (Promega, E1501).
DNA quantity 0.2 μg, 0.5 μg FuGENE HD: Gene transfer was performed according to the protocol, and luciferase activity was measured according to the protocol of the luciferase assay system (Promega, E1501).
DNA quantity 0.2 μg, 0.5 μg FuGENE6: Gene transfer was performed according to the protocol, and luciferase activity was measured according to the protocol of the luciferase assay system (Promega, E1501).
DNA quantity 0.2 μg, 0.5 μg (3) Toxicity Evaluation Preceding Day NHDF-ad cells were seeded in a 96-well plate.
(NHDF-ad cells: 3.5×10$^3$ cells/well·DMEM+10% FBS (Pe/St) 70 μl)

Evaluation Day (i) A 20 mM Tris-HCl (pH 7.4) buffer was dispensed into two tubes at, individually, 54.25 μl (for DL-G1) and 35.5 μl (for DL-U2).

(ii) 1.0 μg of plasmid DNA (pEGFP-luc+) was added to each of the two tubes prepared in step (i) at 2 μl (1.0 μg), and the contents were stirred.
(iii) To the prepared plasmid DNA solutions was added 37.5 μl of a DL-U2 liposome solution (N/P ratio=6), and the whole was thoroughly mixed using a vortex and incubated at room temperature for 30 minutes.
(iv) 25 μl of an Opti-MEM(R) I Reduced-Serum Medium was further added, and the whole was thoroughly mixed and allowed to stand at room temperature for 5 minutes.
(v) 2.8 and 7.0 μl per well of the DL-plasmid DNA complex solutions was individually added to three wells, and the contents were mixed (the addition amount was one-seventh the addition amount in the luciferase activity measurement).
(vi) The cells were incubated at 37° C. in 5% $CO_2$ for 4 hours, and the growth medium was replaced.
(vii) 48 hours later, toxicity evaluation was performed according to the protocol of a WST-8 kit (Kishida Chemical Co., Ltd.) (a well to which no lipoplex solution was added was defined as 100%).

Lipofectamine LTX: Gene transfer was performed according to the protocol, and toxicity evaluation was performed according to the protocol of a WST-8 kit (Kishida Chemical Co., Ltd.) (a well to which no lipoplex solution was added was defined as 100%).

The addition amount was one-seventh the addition amount in the luciferase activity measurement.

FuGENE HD: Gene transfer was performed according to the protocol, and toxicity evaluation was performed according to the protocol of a WST-8 kit (Kishida Chemical Co., Ltd.) (a well to which no lipoplex solution was added was defined as 100%).

The addition amount was one-seventh the addition amount in the luciferase activity measurement.

FuGENE6: Gene transfer was performed according to the protocol, and toxicity evaluation was performed according to the protocol of a WST-8 kit (Kishida Chemical Co., Ltd.) (a well to which no lipoplex solution was added was defined as 100%).

The addition amount was one-seventh the addition amount in the luciferase activity measurement.

4. Results

The results are shown in FIGS. 16 (GFP expression), 17 (luciferase activity measurement), and 18 (toxicity evaluation).

The use of the commercially available transfer agent hardly allowed the GFP gene to be transferred into the normal epithelial cells derived from adult humans. In contrast, it is found that the use of the polyamidoamine dendron of the present invention allowed the gene to be transferred into the cells at a remarkably high frequency.

The polyamidoamine dendron of the present invention was compared with the commercially available transfer agents with respect to cytotoxicity in the case where the GFP gene was transferred to the normal epithelial cells derived from adult humans. As a result, the toxicity of the polyamidoamine dendron of the present invention was lower than those of most of the commercially available transfer agents. Of the commercially available transfer agents, FuGENE6 had relatively low toxicity, but extremely low gene transfer efficiency. It is found that the polyamidoamine dendron of the present invention is particularly excellent in terms of providing both high gene transfer efficiency and low cytotoxicity, even when compared with commercially available transfer agents.

Example 7

Gene Transfer (6)

DL-U2, which was obtained in Example 1, and a commercially available gene transfer agent were compared as described below.

pEGFP-C1 expressing a green fluorescent protein was used as a gene transfer plasmid, and NHDF-ad cells, which were normal epithelial cells derived from adult humans also used for production of iPS cells, were used as target cells. Lipoplexes were individually prepared using DL-U2. Then, gene transfer was performed multiple times.

Specifically, the following procedures were employed.

The lipoplexes were prepared in the same manner as in Example 3.

1. Method
(1) Expression of GFP
Preceding Day
NHDF-ad cells were seeded in a 24-well plate.
(NHDF-ad cells: $2 \times 10^4$ cells/well·DMEM+10% FBS (Pe/St) 500 μl)
Day 1
(i) A 20 mM Tris-HCl (pH 7.4) buffer was dispensed into tubes at 71 μl (for NP ratio=6).
(ii) 2.0 μg of plasmid DNA (pCAG-GFP) were added to each of the two tubes prepared in step (i) at 4 μl (2.0 μg), and the contents were stirred.
(iii) To the prepared plasmid DNA solution was added 75 μl of a DL-U2 liposome solution (N/P ratio=6), and the whole was thoroughly mixed using a vortex and incubated at room temperature for 30 minutes.
(iv) 50 μl of an Opti-MEM(R) I Reduced-Serum Medium was further added, and the whole was thoroughly mixed and allowed to stand at room temperature for 5 minutes.
(v) 100 μl per well of the DL-plasmid DNA complex solutions was individually added to one well, and the contents were mixed by shaking the plate so as to be homogeneous.
(vi) The cells were incubated at 37° C. in 5% $CO_2$ for 4 hours, and the growth medium was replaced.

For the cells subjected to gene transfer operations on Day 1, the same gene transfer was performed on Day 3 and Day 5 as well.

Day 7 GFP-expressing cells were observed with a fluorescence microscope (Olympus, CKX41) (observed at a magnification of 40×).

Lipofectamine LTX: Gene transfer was performed for the same cells on Day 1, Day 3, and Day 5 according to the protocol; and GFP-expressing cells were observed with a fluorescence microscope (Olympus, CKX41) on Day 7.
(observed at a magnification of 100×)
DNA Quantity 1.0 μg FuGENE HD: Gene transfer was performed for the same cells on Day 1, Day 3, and Day 5 according to the protocol; and GFP-expressing cells were observed with a fluorescence microscope (Olympus, CKX41) on Day 7.
(observed at a magnification of 100×)
DNA Quantity 1.0 μg FuGENE6: Gene transfer was performed for the same cells on Day 1, Day 3, and Day 5 according to the protocol; and GFP-expressing cells were observed with a fluorescence microscope (Olympus, CKX41) on Day 7.
(observed at a magnification of 100×)
DNA quantity 1.0 μg (2) Toxicity Evaluation
Preceding Day
NHDF-ad cells were seeded in a 96-well plate.
(NHDF-ad cells: $3.5 \times 10^3$ cells/well·DMEM+10% FBS (Pe/St) 70 μl)

Day 1
(i) A 20 mM Tris-HCl (pH 7.4) buffer was dispensed into tubes at 35.5 μl (for NP ratio=6).
(ii) 1.0 μg of plasmid DNA (pCAG-GFP) was added to each of the two tubes prepared in step (i) at 2 μl (1.0 μg), and the contents were stirred.
(iii) To the prepared plasmid DNA solution was added 37.5 μl of a DL-U2 liposome solution (N/P ratio=6), and the whole was thoroughly mixed using a vortex and incubated at room temperature for 30 minutes.
(iv) 25 μl of an Opti-MEM(R) I Reduced-Serum Medium was further added, and the whole was thoroughly mixed and allowed to stand at room temperature for 5 minutes.
(v) The addition amount was one-seventh the addition amount in the luciferase activity measurement.

7 μl and 14 μl per well of the DL-plasmid DNA complex solutions was individually added to three wells, and the contents were mixed by shaking the plate so as to be homogeneous.
(vi) The cells were incubated at 37° C. in 5% $CO_2$ for 4 hours, and the growth medium was replaced.

For the cells subjected to gene transfer operations on Day 1, the same gene transfer was performed on Day 3 and Day 5, as well.
Day 7 Toxicity evaluation was performed according to the protocol of a WST-8 kit (Kishida Chemical Co., Ltd.).
(a well to which no lipoplex solution was added was defined as 100%)
Lipofectamine LTX: Gene transfer was performed for the same cells on Day 1, Day 3, and Day 5 according to the protocol; and toxicity evaluation was performed on Day 7 according to the protocol of a WST-8 kit (Kishida Chemical Co., Ltd.) (a well to which no lipoplex solution was added was defined as 100%).

The addition amount was one-seventh the addition amount in the luciferase activity measurement.

FuGENE HD: Gene transfer was performed for the same cells on Day 1, Day 3, and Day 5 according to the protocol; and toxicity evaluation was performed on Day 7 according to the protocol of a WST-8 kit (Kishida Chemical Co., Ltd.) (a well to which no lipoplex solution was added was defined as 100%).

The addition amount was one-seventh the addition amount in the luciferase activity measurement.

FuGENE6: Gene transfer was performed for the same cells on Day 1, Day 3, and Day 5 according to the protocol; and toxicity evaluation was performed on Day 7 according to the protocol of a WST-8 kit (Kishida Chemical Co., Ltd.) (a well to which no lipoplex solution was added was defined as 100%).

The addition amount was one-seventh the addition amount in the luciferase activity measurement.

2. Results
The results are shown in FIGS. 19 (GFP expression) and 20 (toxicity evaluation). Each of these figures shows data obtained after a lapse of 7 days from the first transfection.

Production of iPS cells requires multiple gene transfers. Assuming such a situation, the polyamidoamine dendron of the present invention was compared with a commercially available vector with respect to effects obtained in the case where gene transfer into normal epithelial cells derived from adult humans was performed multiple times. FuGENE 6 did not show any gene transfer activity. The polyamidoamine dendron of the present invention not only allowed the gene to be expressed most efficiently, but also had the lowest toxicity. Therefore, it is found that the polyamidoamine dendron of the present invention is also particularly excellent in terms of the gene transfer agent that may be used for production of iPS cells.

Example 8

Gene Transfer (7)

Transfection of various cell strains using DL-U2, which was obtained in Example 1, was performed as described below.

1. Method

The conditions of transfection were as shown in Table 1. 4 hours after the addition, the medium was replaced (however, the medium was not replaced for Jurkat, K562). 48 hours later, GFP-expressing cells were observed with a fluorescence microscope (Olympus, CKX41). It should be noted that experimental conditions not described in the table conformed to those of the other examples.

TABLE 1

| Cell type | Number of cells (24-well plate) | DNA-Tris solution | DL-U2 | Opti-MEM | Addition amount |
|---|---|---|---|---|---|
| COS7 | $2 \times 10^4$/500 μl DMEM | 1.0 μg/37.5 μl | 37.5 μl | 25 μl | 100 μl/well |
| HeLa-S3 | $3 \times 10^4$/500 μl DMEM | 1.0 μg/37.5 μl | 37.5 μl | 25 μl | 100 μl/well |
| A549 | $3 \times 10^4$/500 μl DMEM | 1.0 μg/37.5 μl | 37.5 μl | 25 μl | 100 μl/well |
| U2OS | $2.5 \times 10^4$/500 μl DMEM | 1.0 μg/50 μl | 25 μl | 25 μl | 100 μl/well |
| SKOV3 | $2.5 \times 10^4$/500 μl RPMI | 1.0 μg/37.5 μl | 37.5 μl | 25 μl | 100 μl/well |
| Balb3T3 | $2.5 \times 10^4$/500 μl DMEM | 1.0 μg/50 μl | 25 μl | 25 μl | 100 μl/well |
| CHO | $3 \times 10^4$/500 μl F-12 HAM | 1.0 μg/37.5 μl | 37.5 μl | 25 μl | 100 μl/well |
| Jurkat | $1 \times 10^5$/500 μl RPMI | 1.0 μg/37.5 μl | 37.5 μl | 25 μl | 100 μl/well |
| K562 | $1 \times 10^5$/500 μl RPMI | 1.0 μg/37.5 μl | 37.5 μl | 25 μl | 100 μl/well |

2. Results
The results are shown in FIG. 21.
The results show that the polyamidoamine dendron of the present invention allowed the gene to be efficiently transferred into various types of cells.

The invention claimed is:
1. A gene transfer agent composition comprising a compound represented by any one of the following formulae DL-G1 to DL-G4:

$$R^1R^2NX(XH_2)_2; \quad \text{DL-G1:}$$

$$R^1R^2NX(X(XH_2)_2)_2; \quad \text{DL-G2:}$$

$$R^1R^2NX(X(X(XH_2)_2)_2)_2; \quad \text{DL-G3:}$$

and $$R^1R^2NX(X(X(X(XH_2)_2)_2)_2)_2, \quad \text{DL-G4:}$$

where X represents —$CH_2CH_2CONHCH_2CH_2N$—,
wherein:
$R^1$ represents an unsaturated long-chain aliphatic group; and R² represents an unsaturated long-chain aliphatic group or a saturated long-chain aliphatic group in the formulae.

2. The gene transfer agent composition according to claim 1, wherein the long-chain aliphatic group comprises an aliphatic group having 10 to 22 carbon atoms.

3. The gene transfer agent composition according to claim 1, further comprising a phospholipid.

4. The gene transfer agent composition according to claim 3, wherein the phospholipid comprises DOPE.

5. A method of transferring a gene into a cell, comprising applying the gene transfer agent composition according to claim 1 and a gene to a cell in vitro or in vivo, provided that a human is excluded.

6. A gene transfer kit, comprising the gene transfer agent composition according to claim 1.

* * * * *